(12) United States Patent
Pallett et al.

(10) Patent No.: US 7,250,561 B1
(45) Date of Patent: *Jul. 31, 2007

(54) CHIMERA GENE WITH SEVERAL HERBICIDE RESISTANT GENES, PLANT CELL AND PLANT RESISTANT TO SEVERAL HERBICIDES

(75) Inventors: Ken Pallett, Ongar Essex (GB); Richard DeRose, Lyons (FR); Bernard Pelissier, St. Didier au Mont d'Or (FR); Alain Sailland, Lyons (FR)

(73) Assignee: Bayer Cropscience S.A. (FR)

( * ) Notice: Subject to any disclaimer, the term of this patent is extended or adjusted under 35 U.S.C. 154(b) by 0 days.

This patent is subject to a terminal disclaimer.

(21) Appl. No.: 08/945,821

(22) PCT Filed: Jul. 10, 1997

(86) PCT No.: PCT/FR97/01256

§ 371 (c)(1),
(2), (4) Date: Jun. 15, 1998

(87) PCT Pub. No.: WO98/02562

PCT Pub. Date: Jan. 22, 1998

(30) Foreign Application Priority Data

Jul. 16, 1996 (FR) .................................. 96 09137

(51) Int. Cl.
*A01H 5/00* (2006.01)
*C12N 15/82* (2006.01)

(52) U.S. Cl. .................. 800/300; 435/419; 435/320.1; 536/23.2

(58) Field of Classification Search ............... 536/23.2, 536/23.7; 435/320.1, 410; 800/300
See application file for complete search history.

(56) References Cited

U.S. PATENT DOCUMENTS

| | | | |
|---|---|---|---|
| 4,769,061 A | 9/1988 | Comai | 504/206 |
| 5,188,642 A | 2/1993 | Shah et al. | 47/58.1 R |
| 5,530,187 A | 6/1996 | Lamb et al. | 800/279 |
| 5,635,618 A | 6/1997 | Capellades et al. | 800/288 |
| 6,069,115 A * | 5/2000 | Pallett et al. | 504/270 |
| 6,118,050 A * | 9/2000 | Sturner et al. | 800/298 |
| 6,245,968 B1 | 6/2001 | Boudec et al. | |

FOREIGN PATENT DOCUMENTS

| | | |
|---|---|---|
| EP | 0507698 A1 | 10/1992 |
| EP | 0508909 A1 | 10/1992 |
| EP | 0614970 A2 | 2/1994 |
| EP | 0652286 A1 | 5/1995 |
| WO | WO 92/04449 | 3/1992 |
| WO | WO 92/16101 | 10/1992 |
| WO | WO 95/06128 | 8/1994 |
| WO | WO 95/06128 * | 3/1995 |
| WO | WO 95/12669 | 5/1995 |
| WO | WO 96/38567 | 12/1996 |
| WO | WO 97/06269 | 2/1997 |

OTHER PUBLICATIONS

Yang et al 2004, Biochemistry 43: 10414-10423.*
Duggleby 1997, Gene 190:245-249.*
Norris et al., The Plant Cell, 7:2129 (1995).
Newman et al., Plant Phy. 106:1241 (1994).
Ruetschi et al., Euro. J. Biochem. 205:459 (1992).
Secor, Plant Phys.. 106:1429 (1994).
Schultz et al., FEBS 318:162 (1993).
Prisbylla et al., Brighton Crop Protection Conference (1993).
Norris et al., Am. Soc. Plant Phys., Meeting Abstract (1996).
Endo et al., J. Biol. Chem. 267:24235 (1992).
Wintermeyer et al., Inf. & Imm. 62:1109 (1994).
Awata et al., Genomics 23:534 (1994).
Ruzafa et al., FEMS Microbiology Letters 124:179 (1994).
Misawa et al., The Plant Journal 6:481 (1994).
Barta et al., Pesticide Science 45:286 (1995).
Gugi et al., J. Bacteriology 173:3814 (1991).
Fuqua et al., Gene 109:131 (1991).
Denoya et al., J. Bacteriology 176:5312 (1994).
Wyckoff et al., Gene 161:107 (1995).
Lenne et al., from "Photosynthesis:from Light to the Biosphere", pp. 285-288 (1995).
Newman, Sequence AT 952, Accession T 20952, Jun. 26, 1994.
Newman, Sequence AT 76417, Accession N65764, Mar. 8, 1996.
Mazur B. J. et al. "The Development of Herbicide Resistant Crops." Annual Review of Plant Physiology. 1989. vol. 40, pp. 441-470.

* cited by examiner

*Primary Examiner*—David H Kruse
(74) *Attorney, Agent, or Firm*—Connolly Bove Lodge & Hutz LLP

(57) ABSTRACT

1. Chimeric gene containing several herbicide tolerance genes, plant cell and plant which are tolerant to several herbicides.

2. The plant is tolerant to several herbicides at the same time, in particular to the inhibitors of HPPD and to those of EPSPS and/or to the dihalohydroxybenzonitriles.

3. Use for removing weeds from plants with several herbicides.

18 Claims, 4 Drawing Sheets

```
GCNGAYYTNTAYGARAAYCCNATGG  GNYTNATGGGNTTYGARTTYATHGA  RYTNGCNWSNCCNACNCCNAAYACN    75
 A   D   L   Y   E   N   P   M   G    G   N   Y   M   G   L   M   G   F   E   F   I   E    R   Y   T   N   G   C   N   W   S   N   C   C   N   A   C   N   C   C   N   A   A   Y   A   C   N
                                                                  L   A   S   P   T   P   N   T

YTNGARCCNATHTTYGARATHATGG  GNTTYACNAARGTNGCNACNCAYMG  NWSNAARGAYGTNCAYYTNTAYMGN   150
 L   E   P   I   F   E   I   M   G    F   T   K   V   A   T   H   R    S   K   D   V   H   L   Y   R

CARGGNGCNATHAAYYTNATHYTNA  AYAAYGARCCNCAYWSNGTNGCNWS  NTAYTTYGCNGARCAYGGNCCN     225
 Q   G   A   I   N   L   I   L   N    E   P   H   S   V   A   S    Y   F   A   A   E   H   G   P

WSNGTNTGYGGNATGGCNTTYMGNG  TNAARGAYWSNCARAARGCNTAYAA  RMGNGCNYTNGARYTNGGNGCNCAR   300
 S   V   C   G   M   A   F   R   V    K   D   S   Q   K   A   Y   K    R   A   L   E   L   G   A   Q

CCNATHCAYATHGARACNGGNCCNA  TGGARYTNAAYYTNCCNGCNATHAA  RGGNATHGGNGGNGCNCCNYTNTAY   375
 P   I   H   I   E   T   G   P   M    E   L   N   L   P   A   I   K    G   I   G   G   A   P   L   Y

YTNATHGAYMGNTTYGGNARGGNW   SNWSNATHTAYGAYATHGAYTTYGT  NTTYYTNGARGGNGTNGAYMGNCAY   450
 K   I   D   R   F   G   E   G   S    S   I   Y   D   I   D   F   V    F   L   E   G   V   D   R   H

CCNGTNGGNGCNGGNYTNAARATHA  THGAYCAYYTNACNCAYAAYGTNTA  YMGNGGNMGNATGGCNTAYTGGGCN   525
 P   V   G   A   G   L   K   I   I    D   H   L   T   H   N   V   Y    R   G   R   M   A   Y   W   A

AAYTTYTAYGARAARYTNTTYAAYT  TYMGNGARATHMGNTAYTTYGAYAT  HAARGGNGARTAYACNGGNYTNACN   600
 N   F   Y   E   K   L   F   N   F    R   E   I   R   Y   F   D   I    K   G   E   Y   T   G   L   T

WSNAARGCNATGACNGCNCCNGAYG  GNATGATHMGNATHCCNYTNAAYGA  RGARWSNWSNAARGGNGCNGGNCAR   675
 S   K   A   M   T   A   P   D   G    M   I   R   I   P   L   N   E    E   S   S   K   G   A   G   Q

FIG. 1A
```

```
ATHGARGARTTYYTNATGCARTTYA AYGGNGARGGNATHCARCAYGTNGC NTTYYTNWSNGAYGAYTNATHAAR        750
 I  E  E  F  L  M  Q  F  N   G  E  G  I  Q  H  V  A    F  L  S  D  D  L  I  K

ACNTGGAYCAYYTNAARWSNATHG GNATGMGNTTYATGACNGCNCCNCC NGAYACNTAYTAYGARATGYTNGAR        825
 T  W  D  H  L  K  S  I  G   M  R  F  M  T  A  P  P    D  T  Y  Y  E  M  L  E

GGNMGNYTNCCNAAYCAYGGNGARC CNGTNGGNGARYTNCARGCNMGNGG NATHYTNYTNGAYGGNWSNWSNGAR        900
 G  R  L  P  N  H  G  E  P   V  G  E  L  Q  A  R  G    I  L  L  D  G  S  S  E

WSNGGNGAYAARMGNYTNYTNYTNC ARATHTTYWSNGARACNYTATGGG NCCNGTNTTYTTYGARTTYATHCAR        975
 S  G  D  K  R  L  L  L  Q   I  F  S  E  T  L  M  G    P  V  F  F  E  F  I  Q

MGNAARGGNGAYGAYGGNTTYGGNG ARGGNAAYTTYAARGCNYTNTTYGA RWSNATHGARMGNGAYCARGTNMGN       1050
 R  K  G  D  D  G  F  G  E   G  N  F  K  A  L  F  E    S  I  E  R  D  Q  V  R

MGNGGNGTNYTNWSNACNGAY                                                           1071
 R  G  V  L  S  T  D

FIG. 1B
```

```
Consensus          .ADLYENPWG LWGFEFIE.A SPTP.TLEPI FEIMGFTKVA THRSK.VHLY    50
P. fluorescens     M.........  ........F. ....G..... ..........  .....N....    50
Pseudomonas sp.    -.........  ........L. ....N..... ..........  .....D....    49

Consensus          RQG.INLILN NEP.S.ASYF AAEHGPSVCG MAFRVKDSQK AY.RALELGA   100
P. fluorescens     ...E......  ...N.I.... .......... ..........  ..N.......   100
Pseudomonas sp.    ...A......  ...H.V.... .......... ..........  ..K.......    99

Consensus          QPIHI.TGPM ELNLPAIKGI GGAPLYLIDR FGEGSSIYDI DFV.LEGV.R   150
P. fluorescens     .....D....  .......... .......... ..........  ...Y....E.   150
Pseudomonas sp.    .....E....  .......... .......... ..........  ...F....D.   149

Consensus          .PVGAGLX.I DHLTHNVYRG RM.YWANFYE KLFNFRE.RY FDIKGEYTGL   200
P. fluorescens     N.......V.  .......... ..V....... .......A..  ..........   200
Pseudomonas sp.    H.......I.  .......... ..A....... .......I..  ..........   199

Consensus          TSKAM.APDG MIRIPLNEES SKGAGQIEEF LMQFNGEGIQ HVAFL.DDL.   250
P. fluorescens     .....S....  .......... .......... ..........  .....T...V   250
Pseudomonas sp.    .....T....  .......... .......... ..........  .....S...I   249

Consensus          KTWD.LK.IG MRFMTAPPDT YYEHLEGRLP .HGEPY..LQ ARGILLDGSS   300
P. fluorescens     ....A..K..  .......... .......... D.....DQ..  ..........   300
Pseudomonas sp.    ....H..S..  .......... .......... N.....GE..  ..........   299

Consensus          ..GDKRLLLQ IFSETLMGPV FFEFIQRKGD DGFGEGNFKA LFESIERDQV   350
P. fluorescens     VE........  .......... .......... ..........  ..........   350
Pseudomonas sp.    ES........  .......... .......... ..........  ..........   349

Consensus          RRGVL..D                                                    358
P. fluorescens     .....TA.                                                    358
Pseudomonas sp.    .....ST.                                                    357
```

Fig. 3

SEQUENCE LISTING

<160> NUMBER OF SEQ ID NOS: 28

<210> SEQ ID NO 1
<211> LENGTH: 1077
<212> TYPE: DNA
<213> ORGANISM: Pseudomonas fluorescens

<400> SEQUENCE: 1

```
atggcagatc tatacgaaaa cccaatgggc ctgatgggct ttgaattcat cgaattcgcg      60
tcgccgacgc cgggtaccct ggagccgatc ttcgagatca tgggcttcac caaagtcgcg     120
acccaccgtt ccaagaacgt gcacctgtac cgccagggcg agatcaacct gatcctcaac     180
aacgagccca cagcatcgc ctcctacttt gcggccgaac acggcccgtc ggtgtgcggc      240
atggcgttcc gcgtgaagga ctcgcaaaag gcctacaacc gcgccctgga actcggcgcc     300
cagccgatcc atattgacac cgggccgatg gaattgaacc tgccggcgat caagggcatc     360
ggcggcgcgc cgttgtacct gatcgaccgt ttcggcgaag gcagctcgat ctacgacatc     420
gacttcgtgt acctcgaagg tgtggagcgc aatccggtcg gtgcaggtct caaagtcatc     480
gaccacctga cccacaacgt ctatcgcggc cgcatggtct actgggccaa cttctacgag     540
aaattgttca acttccgtga agcgcgttac ttcgatatca agggcgagta caccggcctg     600
acttccaagg ccatgagtgc gccggacggc atgatccgca tcccgctgaa cgaagagtcg     660
tccaagggcg cggggcagat cgaagagttc ctgatgcagt tcaacggcga aggcatccag     720
cacgtggcgt tcctcaccga cgacctggtc aagacctggg acgcgttgaa gaaaatcggc     780
atgcgcttca tgaccgcgcc gccagacact tattacgaaa tgctcgaagg ccgcctgcct     840
gaccacggcg agccggtgga tcaactgcag gcacgcggta tcctgctgga cggatcttcc     900
gtggaaggcg acaaacgcct gctgctgcag atcttctcgg aaaccctgat gggcccggtg     960
ttcttcgaat tcatccagcg caagggcgac gatgggtttg gcgagggcaa cttcaaggcg    1020
ctgttcgagt ccatcgaacg tgaccaggtg cgtcgtggtg tattgaccgc cgattaa      1077
```

<210> SEQ ID NO 2
<211> LENGTH: 1713
<212> TYPE: DNA
<213> ORGANISM: Arabidopsis thaliana

<400> SEQUENCE: 2

```
aatcaatttc acacaggaaa cagctatgac catgattacg aattcgggcc cgggcgcgtg      60
atccggcggc ggcagcggcg gcggcggtgc aggcgggtgc cgaggagatc gtgctgcagc     120
ccatcaagga gatctccggc accgtcaagc tgccggggtc caagtcgctt ccaaccgga      180
tcctcctact cgccgccctg tccgagggga caacagtggt tgataacctg ctgaacagtg     240
aggatgtcca ctacatgctc ggggccttga ggactcttgg tctctctgtc gaagcggaca     300
aagctgccaa aagagctgta gttgttggct gtggtggaaa gttcccagtt gaggatgcta     360
aagaggaagt gcagctcttc ttggggaatg ctggaactgc aatgcggcca ttgacagcag     420
ctgttactgc tgctggtgga aatgcaactt acgtgcttga tggagtacca agaatgaggg     480
agagaccat ggcgacttg gttgtcggat tgaagcagct tggtgcagat gttgattgtt     540
tccttggcac tgactgccca cctgttcgtg tcaatggaat cggagggcta cctggtggca     600
aggtcaagct gtctggctcc atcagcagtc agtacttgag tgccttgctg atggctgctc     660
ctttggctct tggggatgtg gagattgaaa tcattgataa attaatctcc attccgtacg     720
```

-continued

```
tcgaaatgac attgagattg atggagcgtt ttggtgtgaa agcagagcat tctgatagct      780
gggacagatt ctacattaag ggaggtcaaa aatacaagtc ccctaaaaat gcctatgttg      840
aaggtgatgc ctcaagcgca agctatttct tggctggtgc tgcaattact ggagggactg      900
tgactgtgga aggttgtggc accaccagtt tgcagggtga tgtgaagttt gctgaggtac      960
tggagatgat gggagcgaag gttacatgga ccgagactag cgtaactgtt actggcccac     1020
cgcgggagcc atttgggagg aaacacctca aggcgattga tgtcaacatg aacaagatgc     1080
ctgatgtcgc catgactctt gctgtggttg ccctctttgc cgatggcccg acagccatca     1140
gagacgtggc ttcctggaga gtaaaggaga ccgagaggat ggttgcgatc cggacggagc     1200
taaccaagct gggagcatct gttgaggaag gccggactac tgcatcatc acgccgccgg      1260 agaagctgaa cgtgacggcg atcgacacgt acgacgacca caggatggcc atggccttct     1320
cccttgccgc ctgtgccgag gtccccgtca ccatccggga ccctgggtgc acccggaaga     1380
ccttccccga ctacttcgat gtgctgagca ctttcgtcaa gaattaataa agcgtgcgat     1440
actaccacgc agcttgattg aagtgatagg cttgtgctga ggaaatacat ttcttttgtt     1500 ctgttttct cttttcacggg attaagtttt gagtctgtaa cgttagttgt ttgtagcaag     1560
tttctatttc ggatcttaag tttgtgcact gtaagccaaa tttcatttca agagtggttc     1620
gttggaataa taagaataat aaattacgtt tcagtgaaaa aaaaaaaaaa aaaaaaaaa      1680 aaaaaaaaa aaaaaaaaa aacccgggaa ttc                                    1713
```

<210> SEQ ID NO 3
<211> LENGTH: 1340
<212> TYPE: DNA
<213> ORGANISM: Zea mays
<220> FEATURE:
<221> NAME/KEY: CDS
<222> LOCATION: (6)..(1337)

<400> SEQUENCE: 3

```
ccatg gcc ggc gcc gag gag atc gtg ctg cag ccc atc aag gag atc tcc     50
      Ala Gly Ala Glu Glu Ile Val Leu Gln Pro Ile Lys Glu Ile Ser
        1               5                  10                  15 ggc acc gtc aag ctg ccg ggg tcc aag tcg ctt tcc aac cgg atc ctc       98
Gly Thr Val Lys Leu Pro Gly Ser Lys Ser Leu Ser Asn Arg Ile Leu
             20                  25                  30 cta ctc gcc gcc ctg tcc gag ggg aca aca gtg gtt gat aac ctg ctg      146
Leu Leu Ala Ala Leu Ser Glu Gly Thr Thr Val Val Asp Asn Leu Leu
         35                  40                  45 aac agt gag gat gtc cac tac atg ctc ggg gcc ttg agg act ctt ggt      194
Asn Ser Glu Asp Val His Tyr Met Leu Gly Ala Leu Arg Thr Leu Gly
     50                  55                  60 ctc tct gtc gaa gcg gac aaa gct gcc aaa aga gct gta gtt gtt ggc      242
Leu Ser Val Glu Ala Asp Lys Ala Ala Lys Arg Ala Val Val Val Gly
 65                  70                  75 tgt ggt gga aag ttc cca gtt gag gat gct aaa gag gaa gtg cag ctc      290
Cys Gly Gly Lys Phe Pro Val Glu Asp Ala Lys Glu Glu Val Gln Leu
80                  85                  90                  95 ttc ttg ggg aat gct gga act gca atg cgg cca ttg aca gca gct gtt      338
Phe Leu Gly Asn Ala Gly Thr Ala Met Arg Pro Leu Thr Ala Ala Val
                100                 105                 110 act gct gct ggt gga aat gca act tac gtg ctt gat gga gta cca aga      386
Thr Ala Ala Gly Gly Asn Ala Thr Tyr Val Leu Asp Gly Val Pro Arg
            115                 120                 125 atg agg gag aga ccc att ggc gac ttg gtt gtc gga ttg aag cag ctt      434
```

-continued

| | | |
|---|---|---|
| Met Arg Glu Arg Pro Ile Gly Asp Leu Val Val Gly Leu Lys Gln Leu<br>130                             135                      140 | | |
| ggt gca gat gtt gat tgt ttc ctt ggc act gac tgc cca cct gtt cgt<br>Gly Ala Asp Val Asp Cys Phe Leu Gly Thr Asp Cys Pro Pro Val Arg<br>145                             150                      155 | | 482 |
| gtc aat gga atc gga ggg cta cct ggt ggc aag gtc aag ctg tct ggc<br>Val Asn Gly Ile Gly Gly Leu Pro Gly Gly Lys Val Lys Leu Ser Gly<br>160                             165                      170                      175 | | 530 |
| tcc atc agc agt cag tac ttg agt gcc ttg ctg atg gct gct cct ttg<br>Ser Ile Ser Ser Gln Tyr Leu Ser Ala Leu Leu Met Ala Ala Pro Leu<br>                    180                      185                      190 | | 578 |
| gct ctt ggg gat gtg gag att gaa att att gat aaa tta atc tcc att<br>Ala Leu Gly Asp Val Glu Ile Glu Ile Ile Asp Lys Leu Ile Ser Ile<br>               195                      200                      205 | | 626 |
| ccg tac gtc gaa atg aca ttg aga ttg atg gag cgt ttt ggt gtg aaa<br>Pro Tyr Val Glu Met Thr Leu Arg Leu Met Glu Arg Phe Gly Val Lys<br>               210                      215                      220 | | 674 |
| gca gag cat tct gat agc tgg gac aga ttc tac att aag gga ggt caa<br>Ala Glu His Ser Asp Ser Trp Asp Arg Phe Tyr Ile Lys Gly Gly Gln<br>225                             230                      235 | | 722 |
| aaa tac aag tcc cct aaa aat gcc tat gtt gaa ggt gat gcc tca agc<br>Lys Tyr Lys Ser Pro Lys Asn Ala Tyr Val Glu Gly Asp Ala Ser Ser<br>240                             245                      250                      255 | | 770 |
| gca agc tat ttc ttg gct ggt gct gca att act gga ggg act gtg act<br>Ala Ser Tyr Phe Leu Ala Gly Ala Ala Ile Thr Gly Gly Thr Val Thr<br>                    260                      265                      270 | | 818 |
| gtg gaa ggt tgt ggc acc acc agt ttg cag ggt gat gtg aag ttt gct<br>Val Glu Gly Cys Gly Thr Thr Ser Leu Gln Gly Asp Val Lys Phe Ala<br>               275                      280                      285 | | 866 |
| gag gta ctg gag atg atg gga gcg aag gtt aca tgg acc gag act agc<br>Glu Val Leu Glu Met Met Gly Ala Lys Val Thr Trp Thr Glu Thr Ser<br>                    290                      295                      300 | | 914 |
| gta act gtt act ggc cca ccg cgg gag cca ttt ggg agg aaa cac ctc<br>Val Thr Val Thr Gly Pro Pro Arg Glu Pro Phe Gly Arg Lys His Leu<br>305                             310                      315 | | 962 |
| aag gcg att gat gtc aac atg aac aag atg cct gat gtc gcc atg act<br>Lys Ala Ile Asp Val Asn Met Asn Lys Met Pro Asp Val Ala Met Thr<br>320                             325                      330                      335 | | 1010 |
| ctt gct gtg gtt gcc ctc ttt gcc gat ggc ccg aca gcc atc aga gac<br>Leu Ala Val Val Ala Leu Phe Ala Asp Gly Pro Thr Ala Ile Arg Asp<br>                    340                      345                      350 | | 1058 |
| gtg gct tcc tgg aga gta aag gag acc gag agg atg gtt gcg atc cgg<br>Val Ala Ser Trp Arg Val Lys Glu Thr Glu Arg Met Val Ala Ile Arg<br>               355                      360                      365 | | 1106 |
| acg gag cta acc aag ctg gga gca tct gtt gag gaa ggg ccg gac tac<br>Thr Glu Leu Thr Lys Leu Gly Ala Ser Val Glu Glu Gly Pro Asp Tyr<br>                    370                      375                      380 | | 1154 |
| tgc atc atc acg ccg ccg gag aag ctg aac gtg acg gcg atc gac acg<br>Cys Ile Ile Thr Pro Pro Glu Lys Leu Asn Val Thr Ala Ile Asp Thr<br>385                             390                      395 | | 1202 |
| tac gac gac cac agg atg gcc atg gcc ttc tcc ctt gcc gcc tgt gcc<br>Tyr Asp Asp His Arg Met Ala Met Ala Phe Ser Leu Ala Ala Cys Ala<br>400                             405                      410                      415 | | 1250 |
| gag gtc ccc gtc acc atc cgg gac cct ggg tgc acc cgg aag acc ttc<br>Glu Val Pro Val Thr Ile Arg Asp Pro Gly Cys Thr Arg Lys Thr Phe<br>                    420                      425                      430 | | 1298 |
| ccc gac tac ttc gat gtg ctg agc act ttc gtc aag aat taa<br>Pro Asp Tyr Phe Asp Val Leu Ser Thr Phe Val Lys Asn<br>                    435                      440 | | 1340 |

<210> SEQ ID NO 4
<211> LENGTH: 444
<212> TYPE: PRT
<213> ORGANISM: Zea mays

<400> SEQUENCE: 4

```
Ala Gly Ala Glu Glu Ile Val Leu Gln Pro Ile Lys Glu Ile Ser Gly
 1               5                  10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Val Gln Leu Phe
                85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380
```

```
Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
            405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
            435                 440

<210> SEQ ID NO 5
<211> LENGTH: 1340
<212> TYPE: DNA
<213> ORGANISM: Zea mays
<220> FEATURE:
<221> NAME/KEY: CDS
<222> LOCATION: (6)..(1337)

<400> SEQUENCE: 5 ccatg gcc ggc gcc gag gag atc gtg ctg cag ccc atc aag gag atc tcc      50
      Ala Gly Ala Glu Glu Ile Val Leu Gln Pro Ile Lys Glu Ile Ser
      1               5                   10                  15 ggc acc gtc aag ctg ccg ggg tcc aag tcg ctt tcc aac cgg atc ctc        98
Gly Thr Val Lys Leu Pro Gly Ser Lys Ser Leu Ser Asn Arg Ile Leu
            20                  25                  30 cta ctc gcc gcc ctg tcc gag ggg aca aca gtg gtt gat aac ctg ctg       146
Leu Leu Ala Ala Leu Ser Glu Gly Thr Thr Val Val Asp Asn Leu Leu
        35                  40                  45 aac agt gag gat gtc cac tac atg ctc ggg gcc ttg agg act ctt ggt       194
Asn Ser Glu Asp Val His Tyr Met Leu Gly Ala Leu Arg Thr Leu Gly
    50                  55                  60 ctc tct gtc gaa gcg gac aaa gct gcc aaa aga gct gta gtt gtt ggc       242
Leu Ser Val Glu Ala Asp Lys Ala Ala Lys Arg Ala Val Val Val Gly
65                  70                  75 tgt ggt gga aag ttc cca gtt gag gat gct aaa gag gaa gtg cag ctc       290
Cys Gly Gly Lys Phe Pro Val Glu Asp Ala Lys Glu Glu Val Gln Leu
80                  85                  90                  95 ttc ttg ggg aat gct gga atc gca atg cgg tcc ttg aca gca gct gtt       338
Phe Leu Gly Asn Ala Gly Ile Ala Met Arg Ser Leu Thr Ala Ala Val
                100                 105                 110 act gct gct ggt gga aat gca act tac gtg ctt gat gga gta cca aga       386
Thr Ala Ala Gly Gly Asn Ala Thr Tyr Val Leu Asp Gly Val Pro Arg
            115                 120                 125 atg agg gag aga ccc att ggc gac ttg gtt gtc gga ttg aag cag ctt       434
Met Arg Glu Arg Pro Ile Gly Asp Leu Val Val Gly Leu Lys Gln Leu
        130                 135                 140 ggt gca gat gtt gat tgt ttc ctt ggc act gac tgc cca cct gtt cgt       482
Gly Ala Asp Val Asp Cys Phe Leu Gly Thr Asp Cys Pro Pro Val Arg
    145                 150                 155 gtc aat gga atc gga ggg cta cct ggt ggc aag gtc aag ctg tct ggc       530
Val Asn Gly Ile Gly Gly Leu Pro Gly Gly Lys Val Lys Leu Ser Gly
160                 165                 170                 175 tcc atc agc agt cag tac ttg agt gcc ttg ctg atg gct gct cct ttg       578
Ser Ile Ser Ser Gln Tyr Leu Ser Ala Leu Leu Met Ala Ala Pro Leu
                180                 185                 190 gct ctt ggg gat gtg gag att gaa atc att gat aaa tta atc tcc att       626
Ala Leu Gly Asp Val Glu Ile Glu Ile Ile Asp Lys Leu Ile Ser Ile
            195                 200                 205 ccg tac gtc gaa atg aca ttg aga ttg atg gag cgt ttt ggt gtg aaa       674
Pro Tyr Val Glu Met Thr Leu Arg Leu Met Glu Arg Phe Gly Val Lys
        210                 215                 220
```

-continued

```
gca gag cat tct gat agc tgg gac aga ttc tac att aag gga ggt caa      722
Ala Glu His Ser Asp Ser Trp Asp Arg Phe Tyr Ile Lys Gly Gly Gln
225                 230                 235 aaa tac aag tcc cct aaa aat gcc tat gtt gaa ggt gat gcc tca agc      770
Lys Tyr Lys Ser Pro Lys Asn Ala Tyr Val Glu Gly Asp Ala Ser Ser
240                 245                 250                 255 gca agc tat ttc ttg gct ggt gct gca att act gga ggg act gtg act      818
Ala Ser Tyr Phe Leu Ala Gly Ala Ala Ile Thr Gly Gly Thr Val Thr
            260                 265                 270 gtg gaa ggt tgt ggc acc acc agt ttg cag ggt gat gtg aag ttt gct      866
Val Glu Gly Cys Gly Thr Thr Ser Leu Gln Gly Asp Val Lys Phe Ala
        275                 280                 285 gag gta ctg gag atg atg gga gcg aag gtt aca tgg acc gag act agc      914
Glu Val Leu Glu Met Met Gly Ala Lys Val Thr Trp Thr Glu Thr Ser
    290                 295                 300 gta act gtt act ggc cca ccg cgg gag cca ttt ggg agg aaa cac ctc      962
Val Thr Val Thr Gly Pro Pro Arg Glu Pro Phe Gly Arg Lys His Leu
305                 310                 315 aag gcg att gat gtc aac atg aac aag atg cct gat gtc gcc atg act     1010
Lys Ala Ile Asp Val Asn Met Asn Lys Met Pro Asp Val Ala Met Thr
320                 325                 330                 335 ctt gct gtg gtt gcc ctc ttt gcc gat ggc ccg aca gcc atc aga gac     1058
Leu Ala Val Val Ala Leu Phe Ala Asp Gly Pro Thr Ala Ile Arg Asp
            340                 345                 350 gtg gct tcc tgg aga gta aag gag acc gag agg atg gtt gcg atc cgg     1106
Val Ala Ser Trp Arg Val Lys Glu Thr Glu Arg Met Val Ala Ile Arg
        355                 360                 365 acg gag cta acc aag ctg gga gca tct gtt gag gaa ggg ccg gac tac     1154
Thr Glu Leu Thr Lys Leu Gly Ala Ser Val Glu Glu Gly Pro Asp Tyr
    370                 375                 380 tgc atc atc acg ccg ccg gag aag ctg aac gtg acg gcg atc gac acg     1202
Cys Ile Ile Thr Pro Pro Glu Lys Leu Asn Val Thr Ala Ile Asp Thr
385                 390                 395 tac gac gac cac agg atg gcg atg gcc ttc tcc ctt gcc gcc tgt gcc     1250
Tyr Asp Asp His Arg Met Ala Met Ala Phe Ser Leu Ala Ala Cys Ala
400                 405                 410                 415 gag gtc ccc gtc acc atc cgg gac cct ggg tgc acc cgg aag acc ttc     1298
Glu Val Pro Val Thr Ile Arg Asp Pro Gly Cys Thr Arg Lys Thr Phe
            420                 425                 430 ccc gac tac ttc gat gtg ctg agc act ttc gtc aag aat taa             1340
Pro Asp Tyr Phe Asp Val Leu Ser Thr Phe Val Lys Asn
        435                 440
```

<210> SEQ ID NO 6
<211> LENGTH: 444
<212> TYPE: PRT
<213> ORGANISM: Zea mays

<400> SEQUENCE: 6

```
Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Gly Cys
65                  70                  75                  80
```

-continued

```
Gly Gly Lys Phe Pro Val Glu Asp Ala Lys Glu Val Gln Leu Phe
                 85                  90                  95

Leu Gly Asn Ala Gly Ile Ala Met Arg Ser Leu Thr Ala Ala Val Thr
            100                 105                 110

Ala Ala Gly Gly Asn Ala Thr Tyr Val Leu Asp Gly Val Pro Arg Met
            115                 120                 125

Arg Glu Arg Pro Ile Gly Asp Leu Val Val Gly Leu Lys Gln Leu Gly
            130                 135                 140

Ala Asp Val Asp Cys Phe Leu Gly Thr Asp Cys Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Asp Lys Leu Ile Ser Ile Pro
            195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
            275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
            355                 360                 365

Glu Leu Thr Lys Leu Gly Ala Ser Val Glu Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
            435                 440
```

<210> SEQ ID NO 7
<211> LENGTH: 17
<212> TYPE: DNA
<213> ORGANISM: Unknown
<220> FEATURE:
<223> OTHER INFORMATION: oligonucleotide
<220> FEATURE:
<221> NAME/KEY: misc_feature

```
<222> LOCATION: (12)..(12)
<223> OTHER INFORMATION: n is i

<400> SEQUENCE: 7
taygaraayc cnatggg                                                    17

<210> SEQ ID NO 8
<211> LENGTH: 17
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: (6)..(6), (9)..(9), (12)..(12)
<223> OTHER INFORMATION: n is i

<400> SEQUENCE: 8
garacnggnc cnatgga                                                    17

<210> SEQ ID NO 9
<211> LENGTH: 20
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: (9)..(9)
<223> OTHER INFORMATION: n is i

<400> SEQUENCE: 9
aaytgcatna rraaytcytc                                                 20

<210> SEQ ID NO 10
<211> LENGTH: 20
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: (3)..(3), (6)..(6), (18)..(18)
<223> OTHER INFORMATION: n is i

<400> SEQUENCE: 10
aangcnacrt gytgdatncc                                                 20

<210> SEQ ID NO 11
<211> LENGTH: 20
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: (12)..(12), (18)..(18)
<223> OTHER INFORMATION: n is i

<400> SEQUENCE: 11
gcyttraart tnccytcncc                                                 20

<210> SEQ ID NO 12
<211> LENGTH: 78
<212> TYPE: DNA
<213> ORGANISM: Unknown
<220> FEATURE:
<221> NAME/KEY: misc_feature
<222> LOCATION: (1)..(78)
```

-continued

<223> OTHER INFORMATION: oligonucleotide linker

<400> SEQUENCE: 12
aattgggcca gtcaggccgt ttaaaccta gggggcccgc ccggtcagtc cggcaaattt    60
gggatccccc gggcttaa                                                 78

<210> SEQ ID NO 13
<211> LENGTH: 78
<212> TYPE: DNA
<213> ORGANISM: Unknown
<220> FEATURE:
<223> OTHER INFORMATION: oligonucleotide linker

<400> SEQUENCE: 13 agctttttaat taaggcgcgc cctcgagcct ggttcaggga aattaattcc gcgcgggagc    60
tcggaccaag tccctcga                                                 78

<210> SEQ ID NO 14
<211> LENGTH: 20
<212> TYPE: DNA
<213> ORGANISM: Unknown
<220> FEATURE:
<223> OTHER INFORMATION: oligonucleotide

<400> SEQUENCE: 14
gctctgctca tgtctgctcc                                               20

<210> SEQ ID NO 15
<211> LENGTH: 20
<212> TYPE: DNA
<213> ORGANISM: Unknown
<220> FEATURE:
<223> OTHER INFORMATION: oligonucleotide

<400> SEQUENCE: 15
gcccgccctt gacaaagaaa                                               20

<210> SEQ ID NO 16
<211> LENGTH: 10
<212> TYPE: DNA
<213> ORGANISM: Unknown
<220> FEATURE:
<223> OTHER INFORMATION: oligonucleotide

<400> SEQUENCE: 16
aattcccggg                                                          10

<210> SEQ ID NO 17
<211> LENGTH: 6
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: (6)..(6)
<223> OTHER INFORMATION: g is phosphorylated

<400> SEQUENCE: 17 cccggg                                                              6

<210> SEQ ID NO 18
<211> LENGTH: 38
<212> TYPE: DNA
<213> ORGANISM: Unknown

```
<220> FEATURE:
<223> OTHER INFORMATION: 3' terminal end sequence

<400> SEQUENCE: 18
aattaagctc tagagtcgac ctgcaggcat gcaagctt                              38

<210> SEQ ID NO 19
<211> LENGTH: 41
<212> TYPE: DNA
<213> ORGANISM: Unknown
<220> FEATURE:
<223> OTHER INFORMATION: oligonucleotide

<400> SEQUENCE: 19
gagccgagct ccatggccgg cgccgaggag atcgtgctgc a                         41

<210> SEQ ID NO 20
<211> LENGTH: 37
<212> TYPE: DNA
<213> ORGANISM: Unknown
<220> FEATURE:
<223> OTHER INFORMATION: oligonucleotide

<400> SEQUENCE: 20
gcacgatctc ctcggcgccg gccatggagc tcggctc                              37

<210> SEQ ID NO 21
<211> LENGTH: 25
<212> TYPE: DNA
<213> ORGANISM: Unknown
<220> FEATURE:
<223> OTHER INFORMATION: oligonucleotide

<400> SEQUENCE: 21
ccacaggatg gcgatggcct tctcc                                            25

<210> SEQ ID NO 22
<211> LENGTH: 33
<212> TYPE: DNA
<213> ORGANISM: Unknown
<220> FEATURE:
<223> OTHER INFORMATION: oligonucleotide

<400> SEQUENCE: 22
gaatgctgga atcgcaatgc ggccattgac agc                                   33

<210> SEQ ID NO 23
<211> LENGTH: 33
<212> TYPE: DNA
<213> ORGANISM: Unknown
<220> FEATURE:
<223> OTHER INFORMATION: oligonucleotide

<400> SEQUENCE: 23
gaatgctgga actgcaatgc ggtccttgac agc                                   33

<210> SEQ ID NO 24
<211> LENGTH: 34
<212> TYPE: DNA
<213> ORGANISM: Unknown
<220> FEATURE:
<223> OTHER INFORMATION: oligonucleotide

<400> SEQUENCE: 24
cttggggaat gctgccatcg caatgcggcc attg                                  34
```

-continued

<210> SEQ ID NO 25
<211> LENGTH: 36
<212> TYPE: DNA
<213> ORGANISM: Unknown
<220> FEATURE:
<223> OTHER INFORMATION: oligonucleotide

<400> SEQUENCE: 25
ggggaatgct ggaatcgcaa tgcggtcctt gacagc                        36

<210> SEQ ID NO 26
<211> LENGTH: 357
<212> TYPE: PRT
<213> ORGANISM: Pseudomonas sp. strain P.J. 874

<400> SEQUENCE: 26

```
Ala Asp Leu Tyr Glu Asn Pro Met Gly Leu Met Gly Phe Glu Phe Ile
1               5                  10                  15

Glu Leu Ala Ser Pro Thr Pro Asn Thr Leu Glu Pro Ile Phe Glu Ile
            20                  25                  30

Met Gly Phe Thr Lys Val Ala Thr His Arg Ser Lys Asp Val His Leu
        35                  40                  45

Tyr Arg Gln Gly Ala Ile Asn Leu Ile Leu Asn Asn Glu Pro His Ser
    50                  55                  60

Val Ala Ser Tyr Phe Ala Ala Glu His Gly Pro Ser Val Cys Gly Met
65                  70                  75                  80

Ala Phe Arg Val Lys Asp Ser Gln Lys Ala Tyr Lys Arg Ala Leu Glu
                85                  90                  95

Leu Gly Ala Gln Pro Ile His Ile Glu Thr Gly Pro Met Glu Leu Asn
            100                 105                 110

Leu Pro Ala Ile Lys Gly Ile Gly Gly Ala Pro Leu Tyr Lys Ile Asp
        115                 120                 125

Arg Phe Gly Glu Gly Ser Ser Ile Tyr Asp Ile Asp Phe Val Phe Leu
    130                 135                 140

Glu Gly Val Asp Arg His Pro Val Gly Ala Gly Leu Lys Ile Ile Asp
145                 150                 155                 160

His Leu Thr His Asn Val Tyr Arg Gly Arg Met Ala Tyr Trp Ala Asn
                165                 170                 175

Phe Tyr Glu Lys Leu Phe Asn Phe Arg Glu Ile Arg Tyr Phe Asp Ile
            180                 185                 190

Lys Gly Glu Tyr Thr Gly Leu Thr Ser Lys Ala Met Thr Ala Pro Asp
        195                 200                 205

Gly Met Ile Arg Ile Pro Leu Asn Glu Glu Ser Ser Lys Gly Ala Gly
    210                 215                 220

Gln Ile Glu Glu Phe Leu Met Gln Phe Asn Gly Glu Gly Ile Gln His
225                 230                 235                 240

Val Ala Phe Leu Ser Asp Asp Leu Ile Lys Thr Trp Asp His Leu Lys
                245                 250                 255

Ser Ile Gly Met Arg Phe Met Thr Ala Pro Pro Asp Thr Tyr Tyr Glu
            260                 265                 270

Met Leu Glu Gly Arg Leu Pro Asn His Gly Glu Pro Val Gly Glu Leu
        275                 280                 285

Gln Ala Arg Gly Ile Leu Leu Asp Gly Ser Glu Ser Gly Asp Lys
    290                 295                 300

Arg Leu Leu Leu Gln Ile Phe Ser Glu Thr Leu Met Gly Pro Val Phe
305                 310                 315                 320
```

```
Phe Glu Phe Ile Gln Arg Lys Gly Asp Asp Gly Phe Gly Glu Gly Asn
            325                 330                 335

Phe Lys Ala Leu Phe Glu Ser Ile Glu Arg Asp Gln Val Arg Arg Gly
        340                 345                 350

Val Leu Ser Thr Asp
        355

<210> SEQ ID NO 27
<211> LENGTH: 1071
<212> TYPE: DNA
<213> ORGANISM: Artificial sequence
<220> FEATURE:
<223> OTHER INFORMATION: Theoretical nucleotide sequence corresponding
      to the protein sequence of the HPPD from Pseudomonas sp. strain
      P.J. 874
<220> FEATURE:
<221> NAME/KEY: misc_feature
<222> LOCATION: (3)..(228)
<223> OTHER INFORMATION: n located at 3, 9, 21, 27, 30, 36, 54, 57, 60,
      63, 66, 69, 75, 78, 84, 102, 108, 114, 117, 120, 126, 129, 138
      144, 150, 156, 159, 168, 174, 186, 192, 195, 198, 201, 210, 213,
      222, 225 and 228, each n is a, c, g, t/u, unknown or other
<220> FEATURE:
<221> NAME/KEY: misc_feature
<222> LOCATION: (231)..(453)
<223> OTHER INFORMATION: n located at 231, 237,243, 249, 252, 261, 270,
      279, 282, 285, 291, 294, 297, 303, 318, 321, 324, 333, 339, 342,
      345, 354, 360, 363, 366, 369, 372, 378, 387, 393, 399, 402, 405,
      426, 432, 438, 441, 447 and 453,  each n is a, c, g, t/u, unknown
      or other
<220> FEATURE:
<221> NAME/KEY: misc_feature
<222> LOCATION: (456)..(690)
<223> OTHER INFORMATION: n located at 456, 459, 462, 465, 468, 486, 489,
      498, 504, 507, 510, 516, 525, 543, 555, 564, 582, 591, 594, 597,
      600, 603, 609, 615, 618, 621, 627, 636, 642, 645, 657, 660, 666,
      669, 672 and 690, each n is a, c, g, t/u, unknown or other
<220> FEATURE:
<221> NAME/KEY: misc_feature
<222> LOCATION: (705)..(897)
<223> OTHER INFORMATION: n located at 705, 711, 723, 726, 732, 735, 744,
      753, 765, 771, 777, 783, 792, 795, 798, 801, 807, 822, 828, 831,
      834, 837, 846, 852, 855, 858, 864, 870, 873, 876, 882, 885, 891,
      894 and 897, each n is a, c, g, t/u, unknown or other
<220> FEATURE:
<221> NAME/KEY: misc_feature
<222> LOCATION: (903)..(1068)
<223> OTHER INFORMATION: n located at 903, 906, 915, 918, 921, 924, 936,
      942, 945, 951 954, 957, 978, 984, 993, 999, 1005, 1017, 1020,
      1029, 1038, 1047, 1050, 1053, 1056, 1059, 1062, 1065 and 1068,
      each n is a, c, g, t/u, unknown or other

<400> SEQUENCE: 27
gcngayytnt aygaraaycc natgggnytn atgggnttyg arttyathga rytngcnwsn      60
ccnacnccna ayacnytnga rccnathtty garathatgg gnttyacnaa rgtngcnacn    120
caymgnwsna argaygtnca yytntaymgn carggngcna thaayytnat hytnaayaay    180
garccncayw sngtngcnws ntayttygcn gcngarcayg gnccnwsngt ntgyggnatg    240
gcnttymgng tnaargayws ncaraargcn tayaarmgng cnytngaryt nggngcncar    300
ccnathcaya thgaracngg nccnatggar ytnaayytnc cngcnathaa rggnathggn    360
ggngcnccny tntayytnat hgaymgntty ggngarggnw snwsnathta ygayathgay    420
ttygtnttyy tngarggngt ngaymgncay ccngtnggng cnggnytnaa rathathgay    480
cayytnacnc ayaaygtnta ymgnggnmgn atggcntayt gggcnaaytt ytaygaraar    540
ytnttyaayt tymgngarat hmgntaytty gayathaarg gngartayac nggnytnacn    600
wsnaargcna tgacngcncc ngayggnatg athmgnathc cnytnaayga rgarwsnwsn    660
```

```
aarggngcng gncarathga rgarttyytn atgcarttya ayggngargg nathcarcay    720
gtngcnttyy tnwsngayga yytnathaar acntgggayc ayytnaarws nathggnatg    780
mgnttyatga cngcnccncc ngayacntay taygaratgy tngarggnmg nytnccnaay    840
cayggngarc cngtnggnga rytncargcn mgnggnathy tnytngaygg nwsnwsngar    900
wsnggngaya armgnytnyt nytncarath ttywsngara cnytnatggg nccngtntty    960
ttygarttya thcarmgnaa rggngaygay ggnttyggng arggnaaytt yaargcnytn   1020
ttygarwsna thgarmgnga ycargtnmgn mgnggngtny tnwsnacnga y            1071
```

<210> SEQ ID NO 28
<211> LENGTH: 358
<212> TYPE: PRT
<213> ORGANISM: Artificial sequence
<220> FEATURE:
<223> OTHER INFORMATION: Consensus sequence between P. fluorescens and Pseudomonas sp.
<220> FEATURE:
<221> NAME/KEY: misc_feature
<222> LOCATION: (1)..(1)
<223> OTHER INFORMATION: Xaa is Met in P. fluorescens and missing in Pseudomonas sp.
<220> FEATURE:
<221> NAME/KEY: misc_feature
<222> LOCATION: (19)..(19)
<223> OTHER INFORMATION: Xaa is Phe in P. fluorescens and Leu in Pseudomonas sp.
<220> FEATURE:
<221> NAME/KEY: misc_feature
<222> LOCATION: (25)..(25)
<223> OTHER INFORMATION: Xaa is Gly in P. fluorescens and Asn in Pseudomonas sp.
<220> FEATURE:
<221> NAME/KEY: misc_feature
<222> LOCATION: (46)..(46)
<223> OTHER INFORMATION: Xaa is Asn in P. fluorescens and Asp in Pseudomonas sp.
<220> FEATURE:
<221> NAME/KEY: misc_feature
<222> LOCATION: (54)..(54)
<223> OTHER INFORMATION: Xaa is Glu in P. fluorescens and Ala in Pseudomonas sp.
<220> FEATURE:
<221> NAME/KEY: misc_feature
<222> LOCATION: (64)..(64)
<223> OTHER INFORMATION: Xaa is Asn in P. fluorescens and His in Pseudomonas sp.
<220> FEATURE:
<221> NAME/KEY: misc_feature
<222> LOCATION: (66)..(66)
<223> OTHER INFORMATION: Xaa is Ile in P. fluorescens and Val in Pseudomonas sp.
<220> FEATURE:
<221> NAME/KEY: misc_feature
<222> LOCATION: (93)..(93)
<223> OTHER INFORMATION: Xaa is Asn in P. fluorescens and Lys in Pseudomonas sp.
<220> FEATURE:
<221> NAME/KEY: misc_feature
<222> LOCATION: (106)..(106)
<223> OTHER INFORMATION: Xaa is Asp in P. fluorescens and Glu in Pseudomonas sp.
<220> FEATURE:
<221> NAME/KEY: misc_feature
<222> LOCATION: (144)..(144)
<223> OTHER INFORMATION: Xaa is Tyr in P. fluorescens and Phe in Pseudomonas sp.
<220> FEATURE:
<221> NAME/KEY: misc_feature
<222> LOCATION: (149)..(149)
<223> OTHER INFORMATION: Xaa is Glu in P. fluorescens and Asp in Pseudomonas sp.
<220> FEATURE:

-continued

```
<221> NAME/KEY: misc_feature
<222> LOCATION: (151)..(151)
<223> OTHER INFORMATION: Xaa is Asn in P. fluorescens and His in
      Pseudomonas sp.
<220> FEATURE:
<221> NAME/KEY: misc_feature
<222> LOCATION: (159)..(159)
<223> OTHER INFORMATION: Xaa is Val in P. fluorescens and Ile in
      Pseudomonas sp.
<220> FEATURE:
<221> NAME/KEY: misc_feature
<222> LOCATION: (173)..(173)
<223> OTHER INFORMATION: Xaa is Val in P. fluorescens and Ala in
      Pseudomonas sp.
<220> FEATURE:
<221> NAME/KEY: misc_feature
<222> LOCATION: (188)..(188)
<223> OTHER INFORMATION: Xaa is Ala in P. fluorescens and Ile in
      Pseudomonas sp.
<220> FEATURE:
<221> NAME/KEY: misc_feature
<222> LOCATION: (206)..(206)
<223> OTHER INFORMATION: Xaa is Ser in P. fluorescens and Thr in
      Pseudomonas sp.
<220> FEATURE:
<221> NAME/KEY: misc_feature
<222> LOCATION: (246)..(246)
<223> OTHER INFORMATION: Xaa is Thr in P. fluorescens and Ser in
      Pseudomonas sp.
<220> FEATURE:
<221> NAME/KEY: misc_feature
<222> LOCATION: (250)..(250)
<223> OTHER INFORMATION: Xaa is Val in P. fluorescens and Ile in
      Pseudomonas sp.
<220> FEATURE:
<221> NAME/KEY: misc_feature
<222> LOCATION: (255)..(255)
<223> OTHER INFORMATION: Xaa is Ala in P. fluorescens and His in
      Pseudomonas sp.
<220> FEATURE:
<221> NAME/KEY: misc_feature
<222> LOCATION: (258)..(258)
<223> OTHER INFORMATION: Xaa is Lys in P. fluorescens and Ser in
      Pseudomonas sp.
<220> FEATURE:
<221> NAME/KEY: misc_feature
<222> LOCATION: (281)..(281)
<223> OTHER INFORMATION: Xaa is Asp in P. fluorescens and Asn in
      Pseudomonas sp.
<220> FEATURE:
<221> NAME/KEY: misc_feature
<222> LOCATION: (287)..(287)
<223> OTHER INFORMATION: Xaa is Asp in P. fluorescens and Gly in
      Pseudomonas sp.
<220> FEATURE:
<221> NAME/KEY: misc_feature
<222> LOCATION: (288)..(288)
<223> OTHER INFORMATION: Xaa is Gln in P. fluorescens and Glu in
      Pseudomonas sp.
<220> FEATURE:
<221> NAME/KEY: misc_feature
<222> LOCATION: (301)..(301)
<223> OTHER INFORMATION: Xaa is Val in P. fluorescens and Glu in
      Pseudomonas sp.
<220> FEATURE:
<221> NAME/KEY: misc_feature
<222> LOCATION: (302)..(302)
<223> OTHER INFORMATION: Xaa is Glu in P. fluorescens and Ser in
      Pseudomonas sp.
<220> FEATURE:
<221> NAME/KEY: misc_feature
<222> LOCATION: (356)..(356)
<223> OTHER INFORMATION: Xaa is Thr in P. fluorescens and Ser in
      Pseudomonas sp.
<220> FEATURE:
<221> NAME/KEY: misc_feature
<222> LOCATION: (357)..(357)
<223> OTHER INFORMATION: Xaa is Ala in P. fluorescens and Thr in
      Pseudomonas sp.
```

```
<400> SEQUENCE: 28

Xaa Ala Asp Leu Tyr Glu Asn Pro Met Gly Leu Met Gly Phe Glu Phe
1               5                   10                  15

Ile Glu Xaa Ala Ser Pro Thr Pro Xaa Thr Leu Glu Pro Ile Phe Glu
            20                  25                  30

Ile Met Gly Phe Thr Lys Val Ala Thr His Arg Ser Lys Xaa Val His
            35                  40                  45

Leu Tyr Arg Gln Gly Xaa Ile Asn Leu Ile Leu Asn Asn Glu Pro Xaa
        50                  55                  60

Ser Xaa Ala Ser Tyr Phe Ala Ala Glu His Gly Pro Ser Val Cys Gly
65                  70                  75                  80

Met Ala Phe Arg Val Lys Asp Ser Gln Lys Ala Tyr Xaa Arg Ala Leu
            85                  90                  95

Glu Leu Gly Ala Gln Pro Ile His Ile Xaa Thr Gly Pro Met Glu Leu
            100                 105                 110

Asn Leu Pro Ala Ile Lys Gly Ile Gly Ala Pro Leu Tyr Leu Ile
            115                 120                 125

Asp Arg Phe Gly Glu Gly Ser Ser Ile Tyr Asp Ile Asp Phe Val Xaa
            130                 135                 140

Leu Glu Gly Val Xaa Arg Xaa Pro Val Gly Ala Gly Leu Lys Xaa Ile
145                 150                 155                 160

Asp His Leu Thr His Asn Val Tyr Arg Gly Arg Met Xaa Tyr Trp Ala
                165                 170                 175

Asn Phe Tyr Glu Lys Leu Phe Asn Phe Arg Glu Xaa Arg Tyr Phe Asp
            180                 185                 190

Ile Lys Gly Glu Tyr Thr Gly Leu Thr Ser Lys Ala Met Xaa Ala Pro
            195                 200                 205

Asp Gly Met Ile Arg Ile Pro Leu Asn Glu Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Xaa Asp Asp Leu Xaa Lys Thr Trp Asp Xaa Leu
                245                 250                 255

Lys Xaa Ile Gly Met Arg Phe Met Thr Ala Pro Pro Asp Thr Tyr Tyr
            260                 265                 270

Glu Met Leu Glu Gly Arg Leu Pro Xaa His Gly Glu Pro Val Xaa Xaa
            275                 280                 285

Leu Gln Ala Arg Gly Ile Leu Leu Asp Gly Ser Ser Xaa Xaa Gly Asp
            290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
            325                 330                 335

Asn Phe Lys Ala Leu Phe Glu Ser Ile Glu Arg Asp Gln Val Arg Arg
            340                 345                 350

Gly Val Leu Xaa Xaa Asp
            355
```

CHIMERA GENE WITH SEVERAL HERBICIDE RESISTANT GENES, PLANT CELL AND PLANT RESISTANT TO SEVERAL HERBICIDES

The subject of the present invention is a chimeric gene containing several herbicide tolerance genes, a plant cell and a plant which are tolerant to several herbicides.

In the remainder of the description, herbicides will be designated by the common name in particular referenced in "The Pesticide Manual" 10th edition by British Crop Protection Council.

Plants are known which have been transformed so as to be tolerant to certain herbicides such as especially dihalohydroxybenzonitriles, in particular bromoxynil and ioxynil, by means of the gene encoding the nitrilase degrading these herbicides or those tolerant to the EPSPS-inhibiting herbicides, in particular glyphosate, sulfosate or fosametin or tolerant to the acetolactatesynthase (ALS) inhibitors of the sulphonylurea type or to the dihydropteroate synthase inhibitors such as asulam or to the glutamine synthase inhibitors such as glufosinate.

Some herbicides are known, such as the isoxazoles described especially in French Patent Applications 95 06800 and 95 13570 and in particular isoxaflutole, a herbicide which is selective for maize, the diketonitriles such as those described in European Applications 0 496 630, 0 496 631, in particular 2-cyano-3-cyclopropyl-1-(2-$SO_2CH_3$-4-$CF_3$ phenyl)propane-1,3-dione and 2-cyano-3-cyclopropyl-1-(2-$SO_2CH_3$-4-2,3 $Cl_2$ phenyl)propane-1,3-dione, the triketones described in European Applications 0 625 505 and 0 625 508, in particular sulcotrione or those described in U.S. Pat. No. 5,506,195, or the pyrazolinates. Furthermore, the gene encoding the HPPD conferring tolerance to the latter herbicides has been isolated and transgenic plants containing it have been obtained showing a significant tolerance and are the subject of unpublished French Applications No. 95/06800, 95/13570 and 96/05944.

However, agricultural practice shows that farmers like to have, for treating plants and in particular crops, combinations of herbicides, in particular to respond to the various problems of weed removal due to the limits of the herbicide spectrum taken separately. It may be, in addition, advantageous to have a selectable marker gene combined with a herbicide tolerance gene. A need therefore exists for plants and in particular for crops exhibiting tolerance to several herbicides, preferably at least two or three.

It has now been discovered that it is possible to confer multiple herbicide tolerance on a plant cell and on a plant.

The subject of the present invention is first a chimeric gene comprising at least two basic chimeric genes each containing, in the direction of transcription, regulatory elements necessary for its transcription in plants, that is to say at least one regulatory promoter sequence, at least one heterologous coding part comprising a coding sequence encoding an enzyme conferring on plants the tolerance to a herbicide and at least one regulatory terminator sequence or one polyadenylation sequence.

As coding sequence, there may be used in particular all those known to confer on plants tolerance to certain inhibitors such as:

that for EPSPS for tolerance to glyphosate, to sulfosate or to fosametin, in particular those for the mutated or nonmutated protein, there may be mentioned in particular patents: U.S. Pat. No. 4,535,060, EP 115 673, U.S. Pat. No. 4,796,061, U.S. Pat. No. 5,094,945; U.S. Pat. No. 4,971,908, U.S. Pat. No. 5,145,783, EP 293 358; EP 378 985, WO 91/04323; WO 92 044 449; WO 92 06201. In the text which follows, this type of gene will be designated by the sequence or gene "EPSPS".

There may also be mentioned glyphosate oxydoreductase (cf. WO 92/000 377), an enzyme for the detoxification of glyphosate.

that of the gene for the *Klebsiella* sp. nitrilase for tolerance to the dihalobenzonitriles which is described in U.S. Pat. No. 4,810,648 and in particular the gene derived from *Klebsiella ozaenae*, which will be designated in the text which follows by "OXY" gene or sequence, that for HPPD as described in unpublished French Publications No. 95/06800, 95/13570 and 96/05944 which are cited above. This HPPD may be of any type.

More particularly, this sequence may be of bacterial origin, such as in particular the genus *Pseudomonas* or of plant origin, such as in particular a monocotyledonous or dicotyledonous plant, in particular *Arabidopsis* or umbelliferous plants such as for example carrots (*Daucus carota*). It may be a native or a wild-type sequence or possibly mutated while fundamentally retaining a property of herbicide tolerance to HPPD inhibitors, such as the herbicides of the family of isoxazoles or of that of the triketones or the pyrazolinates.

Other sequences may be used:

that for phosphinotricyine acetyl transferase or that for glutamine synthase for tolerance to glufosinate (cf. EP 0 242 236)

that for dihydropteroate synthase for tolerance to asulam (cf. EP 0 369 367)

that for ALS for tolerance to sulphonylureas that for protoporphyrogen oxidase ("protox") for tolerance to herbicides of the family of diphenyl ethers such as acifluorfen or oxyfluorfen or that for the oxadiazoles such as oxadiazon or oxadiargyl and that for the cyclic imides such as chlorophthalim or that for the phenylpyrrazoles such as TNP or that for the pyridines and the phenopylates and carbamate analogues (cf. WO 95/34659).

Preferably, one of the chimeric genes contains a coding sequence for HPPD. In this case, the other sequence(s) may be of any type and may be in particular chosen from the abovementioned group. Preferably, the other sequences are chosen from the group comprising the nitrilase gene for tolerance to the dihalohydroxybenzonitriles and an EPSPS gene.

The chimeric genes according to the invention may, in addition, contain genes encoding properties other than of herbicide tolerance such as, for example, genes for resistance to insects, such as those of the *Bacillus thurigensis* type conferring resistance to various representatives of the coleoptera and lepidoptera family, or genes for resistance to nematodes, genes for resistance to fungal or microbial diseases, or genes conferring agronomic properties such as the genes for the various desaturases involved in the production of fatty acids. There may be mentioned, in particular, that for the delta-6 desaturase described in International Application WO 93/06712.

As regulatory promoter sequence, use may be made of any promoter sequence of a gene which is expressed naturally in plants, in particular a promoter of bacterial, viral or plant origin such as, for example, that of a gene for the small subunit of ribulose biscarboxylase (RuBisCO) or that of a gene for α-tubulin (European Application EP No. 0 652 286), or of a plant virus gene such as, for example, that from the cauliflower mosaic virus (CaMv 19S or 35S), but any known suitable promoter may be used. Preferably, use is made of a regulatory promoter sequence which promotes the overexpression of the coding sequence, such as, for example, that comprising at least one histone promoter as described in European Application EP 0 507 698.

According to the invention, it is also possible to use, in combination with the regulatory promoter sequence, other regulatory sequences which are situated between the promoter and the coding sequence, such as transcription activators, "enhancer", such as for example the tobacco etch virus (TEV) translation activator described in Application WO 87/07644, or transit peptides, either single, or double, and in this case optionally separated by an intermediate sequence, that is to say comprising, in the direction of transcription, a sequence encoding a transit peptide for a plant gene encoding a plastid localization enzyme, a portion of sequence of the N-terminus mature portion of a plant gene encoding a plastid localization enzyme, and then a sequence encoding a second transit peptide for a plant gene encoding a plastid localization enzyme, consisting of a portion of sequence of the N-terminus mature portion of a plant gene encoding a plastid localization enzyme, as described in European Application No. 0 508 909.

As regulatory terminator sequence or polyadenylation sequence, use may be made of any corresponding sequence of bacterial origin, such as for example the *Agrobacterium tumefaciens* nos terminator, or of plant origin, such as for example a histone terminator as described in European Application EP No. 0 633 317.

The subject of the invention is also a plant cell, from monocotyledonous or dicotyledonous plants, especially crops, which is tolerant to at least two herbicides of which at least one is an HPPD inhibitor. This cell may contain at least two chimeric genes each comprising a sequence encoding tolerance to a herbicide and one of which comprises a sequence encoding HPPD. The two chimeric genes may be either carried by the same vector, or each on a different vector, or delivered as such by introducing into the cell by physical or physicochemical means, for example by microinjecton, electroporation or bombardment, according to methods known per se.

The subject of the invention is also a transformed plant which is tolerant to at least two herbicides, one of which is an HPPD inhibitor. This plant may be obtained either by crossing at least two plants each containing a gene encoding tolerance to a herbicide, or by regeneration of a cell according to the invention, as described above. The plants may be monocotyledonous or dicotyledonous, especially crops, major crops such as for example, but with no limitation being implied, for the dicotyledonous plants, tobacco, cotton, rapeseed, soya and beet, and for the monocotyledonous plants maize and straw cereals, or market garden or flower crops.

The subject of the invention is also a process for producing plants with multiple herbicide tolerance by plant transgenesis, characterized in that:
  in a first stage, there is inserted into several cells respectively one of the basic genes each containing regulatory elements necessary for its transcription in plants and a coding sequence encoding an enzyme conferring on plants tolerance to a herbicide, and in that
  the plants are then crossed in order to obtain plants with multiple tolerance.

The subject of the invention is also another process for producing plants with multiple herbicide tolerance by plant transgenesis, a first stage comprising the integration, into plant cells, of at least two genes for tolerance to a herbicide of which at least one is an HPPD inhibitor, the second stage comprising the regeneration of the plant from the transformed cells according to the invention.

The transformation may be obtained by any appropriate means known, widely described in the specialized literature and in particular the patents and applications cited in the present application.

One series of methods consists in bombarding cells or protoplasts with particles to which DNA sequences are attached. According to the invention, these DNAs may be carried by the same particles or by different bombardments. Another series of methods consists in using, as means of transfer into the plant, a chimeric gene inserted into an *Agrobacterium rhizogenes* R1 or *Agrobacterium tumefaciens* Ti plasmid.

Other methods may be used, such as microinjection or electroporation.

Persons skilled in the art will choose the appropriate method according to the nature of the plant, in particular its monocotyledonous or dicotyledonous character.

It has been observed that transformed plants according to the invention exhibit significant tolerance to the hydroxyphenyl pyruvate dioxygenase inhibitors such as some recent herbicides such as the isoxazoles described in particular in French Patent Applications 9 506 800 and 95 13570 and in particular 4-[4-CF3-2-(methylsulphonyl)benzoyl]-5-cyclopropylisoxazole, or "isoxaflutole", a herbicide which is selective for maize, the diketonitriles such as those described in European Applications 0 496 630, 0 496 631, in particular 2-cyano-3-cyclopropyl-1-(2-$SO_2CH_3$-4-$CF_3$ phenyl)propane-1,3-dione and 2-cyano-3-cyclopropyl-1-(2-$SO_2CH_3$-4-2,3 $Cl_2$ phenyl)propane-1,3-dione, the triketones described in European Applications 0 625 505 and 0 625 508, in particular sulcotrione and the pyrazinolates. These same plants according to the invention exhibit significant tolerance to other herbicides such as for example the dihalobenzonitriles, in particular bromoxynil and ioxynil, glyphosate and its analogues, glufosinate.

The subject of the present invention is also the plants regenerated from transformed cells. The regeneration is obtained by any appropriate process which depends on the nature of the species, as for example described in the above applications. The plants according to the invention may also be obtained by crossing parents, each of them carrying one of the genes for herbicide tolerance described.

The subject of the invention is finally a process for removing weed from plants, in particular crops, with the aid of a herbicide of this type, characterized in that this herbicide is applied to transformed plants according to the invention, presowing, preemergence and postemergence of the crop. Herbicide for the purposes of the present invention is understood to mean a herbicidal active substance, alone or combined with an additive which modifies its efficacy, such as for example an agent which increases activity (synergist) or which limits activity (safener).

Of course, for their practical application, the above herbicides are combined, in a manner known per se, with the formulation adjuvants normally used in agricultural chemistry.

According to the invention, one of the herbicide tolerance genes present in the plants may be used as a selectable marker, either in vitro or in vivo.

The various aspects of the invention will be understood more clearly with the aid of the experimental examples below.

EXAMPLE 1

Isolation of the HPPD Gene from *P. fluorescens* A 32

From the amino acid sequence of HPPD from *Pseudomonas* sp. P.J. 874 (published by Rüetschi U. et al. 1992. Eur. J. Biochem. 205: 459-466), the sequence of the different oligonucleotides is deduced so as to amplify, by PCR, a portion of the coding sequence of HPPD from *P. fluorescens* A32 (isolated by McKellar, R. C. 1982. J. Appl. Bacteriol. 53: 305-316). An amplification fragment of the gene for this HPPD was used to screen a *P. fluorescens* A32 partial genomic library and thus to isolate the gene encoding this enzyme.

A) Preparation of the *P. fluorescens* A32 Genomic DNA.

The bacterium was cultured in 40 ml of M63 minimum medium ($KH_2PO_4$ 13.6 g/l, $(NH_4)_2SO_4$ 2 g/l, $MgSO_4$ 0.2 g/l, $FeSO_4$ 0.005 g/l pH 7 plus 10 mM L-tyrosine as sole carbon source) at 28° C. for 48 hours.

After washing, the cells are taken up in 1 ml of lysis buffer (100 mM Tris-HCl pH 8.3, 1.4 M NaCl and 10 mM EDTA) and incubated for 10 minutes at 65° C. After treating with phenol/chloroform (24/1) and treating with chloroform, the nucleic acids are precipitated by addition of one volume of isopropanol and then taken up in 300 µl of sterile water and treated with RNAse 10 µg/ml final. The DNA is again treated with phenol/chloroform, chloroform and reprecipitated by addition of a 1/10 volume of 3 M sodium acetate pH 5 and 2 volumes of ethanol. The DNA is then taken up in sterile water and assayed.

B) Choice of the Oligonucleotides and Syntheses

From the amino acid sequence of the HPPD from *Pseudomonas* sp. P.J. 874, five oligonucleotides are chosen, two are directed in the direction $NH_2$ terminus of the protein towards the COOH terminus of the protein and three directed in the opposite direction (see FIG. 1). The choice was dictated by the following two rules:

a 3' end of the stable oligonucleotide, that is to say at least two bases with no ambiguity, a degeneracy as low as possible.

The chosen oligonucleotides have the following sequences:

P1: 5'TA(C/T)GA(G/A)AA(C/T)CCIATGGG3' (SEQ ID NO:7)

P2: 5'GA(G/A)ACIGGICCIATGGA3' (SEQ ID NO:8)

P3: 5'AA(C/T)TGCATIA(G/A)(G/A)AA(C/T)TC(C/T)TC3' (SEQ ID NO:9)

P4: 5'AAIGCIAC(G/A)TG(C/T)TG(T/G/A)ATICC3' (SEQ ID NO:10)

P5: 5'GC(C/T)TT(A/G)AA(A/G)TTICC(C/T)TCICC3' (SEQ ID NO:11)

They were synthesized on the synthesizer "cyclone plus DNA synthesizer" of MILLPORE brand.

With these five oligonucleotides, by PCR, the amplification fragments which should be theoretically obtained according to the sequence SEQ ID No. 1 have the following sizes:

with the primers P1 and P3→about 690 bp
with the primers P1 and P4→about 720 bp
with the primers P1 and P5→about 1000 bp
with the primers P2 and P3→about 390 bp
with the primers P2 and P4→about 420 bp
with the primers P2 and P5→about 700 bp C) Amplification of a Coding Portion of the HPPD from *P. fluorescens* A32

The amplifications were carried out on a PERKIN ELMER 9600 PCR apparatus and with the PERKIN ELMER Taq polymerase with its buffer, under standard conditions, that is to say for 50 µl of reaction, there are the dNTPs at 200 µM, the primers at 20 µM, the Taq polymerase 2.5 units and the DNA from *P. fluorescens* A32 2.5 µg.

The amplification programme used is 5 min at 95° C., then 35 cycles <45 sec 95° C., 45 sec 49° C., 1 min 72'C> followed by 5 min at 72° C.

Under these conditions, all the amplification fragments obtained have a size which is compatible with the theoretical sizes given above, which is a good indication of the specificity of the amplifications.

The amplification fragments obtained with the pairs of primers P1/P4, P1/P5 and P2/P4 are ligated into pBSII SK(–) after digesting this plasmid with EcoRV and treating with terminal transferase in the presence of ddTTP as described in HOLTON T. A. and GRAHAM M. W., 1991, N.A.R., Vol. 19, No. 5, p. 1156.

A clone of each of the three types is partially sequenced; this makes it possible to confirm that in the three cases, part of the coding region of the HPPD from *P. fluorescens* A32 has indeed been amplified. The P1/P4 fragment is retained as probe in order to screen a *P. fluorescens* A32 partial genomic library and to isolate the complete HPPD gene.

D) Isolation of the Gene

By Southern, it is shown that a 7 Kbp fragment, after digestion of the *P. fluorescens* A32 DNA with the restriction enzyme BamHI, hybridizes with the HPPD P1/P4 probe. 400 µg of *P. fluorescens* A32 DNA were therefore digested with the restriction enzyme BamHI and the DNA fragments of about 7 Kbp were purified on agarose gel.

These fragments are ligated into pBSII SK(–), itself digested with BamHI and dephosphorylated by treating with alkaline phosphatase. After transformation in *E. coli* DH10b, the partial genomic library is screened with the HPPD P1/P4 probe.

A positive clone was isolated and called pRP A. Its simplified map is given in FIG. 2. The position of the coding part of the HPPD gene is indicated on this map. It is composed of 1077 nucleotides which encode 358 amino acids (see SEQ ID No. 1). The HPPD from *P. fluorescens* A32 exhibits good amino acid homology with that from *Pseudomonas* sp. strain P.J. 874; there is indeed 92% identity between these two proteins (see FIG. 3).

EXAMPLE 2

Construction of two Chimeric Genes with an HPPD Sequence

To confer on plants tolerance to herbicides which inhibit HPPD, two chimeric genes are constructed:

The first consists in placing the coding part of the HPPD gene from *P. fluorescens* A32 under the control of the double histone promoter (European Patent Application No. 0 507 698) followed by the tobacco etch virus translational enhancer (TEV) (PRTL-GUS (Carrington and Freed, 1990; J. Virol. 64: 1590-1597)) with the terminator of the nopaline synthase gene. The HPPD will then be located in the cytoplasm.

The second will be identical to the first, the only difference being that between the TEV translation activator and the coding portion of HPPD, the optimized transit peptide (OTP) is intercalated (European Application EP No. 0 508 909). The HPPD will then be located in the chloroplast.

A) Construction of the Vector pRPA-RD-153:

pRPA-RD-11: a derivative of pBS-II SK(−) (Stratagene catalogue #212206) containing the nopaline synthase polyadenylation site (NOS polyA) (European Application No. 0 652 286) is cloned between the KpnI and SalI sites. The KpnI site is converted to an NotI site by treating with T4 DNA polymerase I in the presence of 150 µM deoxynucleotide triphosphates, followed by ligation with an NotI linker (Stratagene catalogue #1029). Thus, an NOS polyA cloning cassette is obtained.

pRPA-RD-127: a derivative of pRPA-BL-466 (European Application EP No. 0 337 899) cloned into pRPA-RD-11 creating a cassette for expression of the oxy gene and containing the promoter of the ribulose biscarboxylase small subunit:

"promoter (SSU)-oxy gene-NOS polyA"

To create this plasmid, pRPA-BL-488 was digested with XbaI and HindIII in order to isolate a 1.9 kbp fragment containing the SSU promoter and the oxy gene, which was ligated into the plasmid pRPA-RD-11 digested with compatible enzymes.

pRPA-RD-132: it is a derivative of pRPA-BL-488 (European Application EP No. 0 507 698) cloned into pRPA-RD-127 with creation of a cassette for expression of the oxy gene with the double histone promoter:

"double histone promoter-oxy gene-NOS polyA"

To manufacture this plasmid, pRPA-BL-466 is digested with HindIII, treated with Klenow and then redigested with NcoI. The purified 1.35 kbp fragment containing the double histone promoter H3A748 is ligated with the plasmid pRPA-RD-127 which had been digested with XbaI, treated with Klenow and redigested with NcoI.

pRPA-RD-153: it is a derivative of pRPA-RD-132 containing the tobacco etch virus (TEV) translation activator. pRTL-GUS (Carrington and Freed. 1990; J. Virol. 64: 1590-1597) is digested with NcoI and EcoRI and the 150 bp fragment is ligated into pRPA-RD-132 digested with the same enzymes. An expression cassette containing the promoter has therefore been created:

"double histone promoter-TEV-oxy u-NOS polyA"

B) Construction of the Vector pRPA-RD-185:

pUC19/GECA: a derivative of pUC-19 (Gibco catalogue #15364-011) containing numerous cloning sites. pUC-19 is digested with EcoRI and ligated with the oligonucleotide linker 1:

Linker 1: AATTGGGCCA GTCAGGCCGT TTAAAC-CCTA GGGGGCCCG CCCGGT CAGTCCGGCA AATTTGGGAT CCCCCGGGC TTAA (SEQ ID NO:12)

The clone selected contains an EcoRI site followed by the polylinker which contains the following sites: EcoRI, ApaI, AvrII, PmeI, SfiI, SacI, KpnI, SmaI, BamHI, XbaI, SalI, PstI, SphI and HindIII.

pRPA-RD-185: it is a derivative of pUC19/GECA containing a modified polylinker. pUC19/GECA is digested with HindIII and ligated with the linker oligonucleotide 2:

Linker 2: AGCTTTTAAT TAAGGCGCGC CCTC-GAGCCT GGTTCAGGG AAATTA ATTCCGCGCG GGAGCTCGGA CCAAGTCCC TCGA (SEQ ID NO:13)

The clone selected contains a HindIII site in the middle of the polylinker which now contains the following sites: EcoRI, ApaI, AvrII, PmeI, SfiI, SacI, KpnI, SmaI, BamHI, XbaI, SalI, PstI, SphI, HindIII, PacI, AscI, XhoI and EcoNI.

C) Construction of the Vector pRP T:

pRP O: a derivative of pRPA-RD-153 containing an HPPD expression cassette, double histone promoter-TEV-HPPD gene-Nos terminator. To manufacture pRP 0, pRPA-RD153 is digested with HindIII, treated with Klenow and then redigested with NcoI in order to remove the oxy gene and to replace it with the HPPD gene derived from the plasmid pRP A by digesting with BstEII, treating with Klenow and redigesting with NcoI.

pRP R: to obtain the plasmid, pRP 0 was digested with PvuII and SacI, the chimeric gene was purified and then ligated into pRPA-RD-185, itself digested with PvuII and SacI.

pRP T: it was obtained by ligating the chimeric gene derived from pRP R after digesting with SacI and HindIII into the plasmid PRPA-BL 150 alpha2 digested with the same enzymes (European Application EP No. 0 508 909).

The chimeric gene of the vector pRP T therefore has the following structure:

| Double histone promoter | TEV | Coding region of HPPD | Nos terminator |
| --- | --- | --- | --- |

D) Construction of the Vector pRP V pRP P: it is a derivative of pRPA-RD-7 (European Application EP No. 0 652 286) containing the optimized transit peptide followed by the HPPD gene. It was obtained by ligating the coding portion of HPPD derived from pRP A by BstEII and NcoI digestion, treatment with Klenow and of the plasmid pRPA-RD-7 itself digested with SphI and AccI and treated with T4 DNAse polymerase.

pRP Q: a derivative of pRPA-RD-153 containing an HPPD expression cassette, double histone promoter-TEV-OTP-HPPD gene-Nos terminator. To construct it, the plasmid pRPA-RD-153 is digested with SalI, treated with Klenow and then redigested with NcoI in order to remove the oxy gene and replace it with the HPPD gene derived from the plasmid pRP P by BstEII digestion, treatment with Klenow and redigestion with NcoI.

pRP S: to obtain it, the plasmid pRP Q was digested with PvuII and SacI in order to remove the chimeric gene which was ligated into pRPA-RD-185 itself digested with PvuII and SacI.

pRP V: it was obtained by ligation of the chimeric gene derived from pRP S after digestion with SacI and HindIII into the plasmid PRPA-BL 150 alpha2 (European Application EP No. 0 508 909).

The chimeric gene of the vector pRP Q therefore has the following structure:

| Double histone promoter | TEV | OTP | Coding region of HPPD | Nos terminator |
| --- | --- | --- | --- | --- |

EXAMPLE 3

Transformation of the Industrial Tobacco PBD6

To determine the efficiency of these two chimeric genes, they were transferred into the industrial tobacco PBD6 according to the transformation and regeneration techniques already described in European Application EP No. 0 508 909.

1) Transformation:

The vector is introduced into the non oncogenic *Agrobacterium* EHA 101 strain (Hood et al., 1987) carrying the cosmid pTVK 291 (Komari et al., 1986). The transformation technique is based on the procedure by Horsh R. et al., (1985) Science, 227, 1229-1231.

2) Regeneration:

The regeneration of the PBD6 tobacco (source SEITA France) from foliar explants is carried out on a Murashige and Skoog (MS) basal medium comprising 30 g/l of sucrose and 100 µg/ml of kanamycin. The foliar explants are removed from greenhouse plants or in vitro and transformed according to the foliar disc technique (Science 1985, Vol. 227, p. 1229-1231) in three successive stages: the first comprises the induction of shoots on an MS medium supplemented with 30 g/l of sucrose containing 0.05 mg/l of naphthylacetic acid (ANA) and 2 mg/l of benzylaminopurine (BAP) for 15 days. The shoots formed during this stage are then developed by culturing on an MS medium supplemented with 30 g/l of sucrose but containing no hormone, for 10 days. Some of the shoots that have developed are then removed and they are cultured on MS rooting medium with half the content of salts, vitamins and sugars and containing no hormone. After about 15 days, the rooted shoots are planted in the soil. The plants obtained are called Co 17.

Upon leaving in vitro, the transformed tobacco plantlets were acclimatized in a greenhouse (60% relative humidity, temperature: 20° C. at night and 23° C. during the day) for five weeks and then treated with 4-[4-$CF_3$-2-(methylsulphonyl)benzoyl]-5-cyclopropylisoxazole.

The control tobacco, not transformed and treated with 4-[4-$CF_3$-2-(methylsulphonyl)benzoyl]-5-cyclopropylisooxazole at doses ranging from 50 to 400 g/ha, develop chlorosis in about 72 hours, which intensifies and develops into very pronounced necrosis within one week (covering about 80% of the terminal leaves).

After transformation, this same tobacco, which overexpresses the *P. fluorescens* HPPD, is very well protected against treatment with 4-[4-$CF_3$-2-(methylsulphonyl)benzoyl]-5-cyclopropylisooxazole at a dose of 400 g/ha.

If the enzyme overexpressed is in the chloroplast, that is to say if the transformation was made with the gene carried by the vector pRP V, then the plant is perfectly protected and shows no symptom.

EXAMPLE 4

Transformation of the Industrial Tobacco PBD6 with EPSPS Gene for ⇒Construct 173

Isolation of a cDNA encoding a maize EPSPS:

The various stages which led to the production of maize EPSPS cDNA, which served as substrate for the introduction of the two mutations, are described below. All the operations described below are given by way of examples and correspond to a choice made among the various methods available to arrive at the same result. This choice has no effect on the quality of the result and, consequently, any suitable method may be used by persons skilled in the art to arrive at the same result. Most of the methods for engineering DNA fragments are described in "Current Protocols in Molecular Biology" Volumes 1 and 2, Ausubel F. M. et al., published by Green Publishing Associates and Wiley-Interscience (1989) (in the text that follows, the references to the protocols described in this manual will be noted "ref. CPMB"). The operations regarding the DNA, which were carried out according to the protocols described in this manual are, in particular, the following: ligation of the DNA fragments, treatments with Klenow DNA polymerase and T4 DNA polymerase, preparation of DNA from plasmids and λ bacteriophages, either as a minipreparation or as a maxipreparation, analyses of DNA and RNA according to the Southern and Northern techniques respectively. Other methods described in this manual were followed and only significant modifications or additions to these protocols have been described below:

A1. Production of an EPSPS fragment from *Arabidopsis thaliana* a) Two 20-mer oligonucleotides of respective sequences:
5'-GCTCTGCTCATGTCTGCTCC-3' (SEQ ID NO:14)
5'-GCCCGCCCTTGACAAAGAAA-3' (SEQ ID NO:15)

were synthesized from the sequence of an *Arabidopsis thalliana* EPSPS gene (Klee H. J. et al. (1987) Mol. Gen. Genet., 210, 437-442). These two oligonucleotides are respectively at position 1523 to 1543 and 1737 to 1717 of the published sequence and in convergent orientation.

were synthesized from the sequence of an *Arabidopsis thaliana* EPSPS gene (Klee H. J. et al. (1987) Mol. Gen. Genet., 210, 437-442). These two oligonucleotides are respectively at position 1523 to 1543 and 1737 to 1717 of the published sequence and in convergent orientation.

b) The total DNA from *Arabidopsis thaliana* (var. *columbia*) was obtained from Clontech (catalogue reference: 6970-1)

c) 50 nanograms (ng) of DNA are mixed with 300 ng of each of the oligonucleotides and subjected to 35 amplification cycles with a Perkin-Elmer 9600 apparatus, under standard medium conditions for amplification which are recommended by the supplier. The resulting 204 bp fragment constitutes the *Arabidopsis thaliana* EPSPS fragment.

2. Construction of a cDNA Library from a BMS Maize Cell Line.

a) 5 g of filtered cells are ground in liquid nitrogen and the total nucleic acids extracted according to the method described by Shure et al., with the following modifications:

the pH of the lysis buffer is adjusted to pH=9.0;

after precipitation with isopropanol, the pellet is taken up in water and after dissolution, adjusted to 2.5 M LiCl. After incubation for 12 h at [lacuna]° C., the 15-min centrifugation pellet at 30,000 g and 4° C. is resolubilized. The precipitation stage with LiCl is then repeated. The resolubilized pellet constitutes the RNA fraction of the total nucleic acids.

b) The RNA-polyA+ fraction of the RNA fraction is obtained by chromatography on an oligo-dT cellulose column as described in "Current Protocols in Molecular Biology".

c) Synthesis of double-stranded cDNA with synthetic EcoRI end: it is performed according to the protocol of the supplier of the various reagents necessary for this synthesis in the form of a kit: the "copy kit" from the company In Vitrogen.

Two single-stranded and partially complementary oligonucleotides of respective sequences:
5'-AATTCCCGGG-3' (SEQ ID NO:16)
5'-CCCGGG-3' (the latter being phosphorylated) (SEQ ID NO:17) are ligated with the blunt ended double-stranded cDNA.

This ligation of the adaptors results in the creation of SmaI sites attached to the double-stranded cDNA and of EcoRI sites in cohesive form at each end of the double-stranded cDNA.

d) Creation of the Library:

The cDNAs having the cohesive artificial EcoRI sites at their ends are ligated with the cDNA from the bacteriophage Xgt10 cut with EcoRI and dephosphorylated according to the protocol from the supplier New England Biolabs.

One aliquot of the ligation reaction was encapsidated in vitro with encapsidation extracts: Gigapack Gold according to the instructions of the supplier, this library was titrated using the bacterium E. coli C600hfl. The library thus obtained is amplified and stored according to the instructions of the same supplier and constitutes the BMS maize cell suspension cDNA library.

3. Screening of the BMS Maize Cell Suspension cDNA Library with the Arabidopsis thaliana EPSPS Probe:

The protocol followed is that of "Current Protocols in Molecular Biology" Volumes 1 and 2, Ausubel F. M. et al., published by Greene Publishing Associates and S (1989) (CPMB). Briefly, about $10^6$ recombinant phages are plated on an LB dish at an average density of 100 phages/cm$^2$. The lysis plaques are subcultured in duplicate on an Amersham Hybond N membrane.

h) The DNA was fixed on the filters by a 1600 kJ UV treatment (Stratalinker from Stratagene). The filters were prehybridized in: 6×SSC/0.1% SDS/0.25 skimmed milk for 2 h at 65° C. The Arabidopsis thaliana EPSPS probe was labelled with $^{32}$P-dCTP by "random priming" according to the instructions of the supplier (Kit Ready to Go from Pharmacia). The specific activity obtained is of the order of $10^8$ cpm per μg of fragment. After denaturation for 5 min at 100° C., the probe is added to the prehybridization medium and the hybridization is continued for 14 hours at 55° C. The filters are fluorographed for 48 h at −80° C. and with a Kodak XAR5 film and Amersham Hyperscreen RPN intensifying screens. The alignment of the positive spots on the filter with the dishes from which they are derived makes it possible to remove, from the dish, zones corresponding to the phages exhibiting a positive hybridization response with the Arabidopsis thaliana EPSPS probe. This plating, transfer, hybridization and recovery stage is repeated until all the spots on the dish of phages successively purified prove 100% positive in hybridization. One lysis plaque per independent phage is then removed from the diluent λ medium (Tris-Cl pH=7.5; 10 mM MgSO$_4$; 0.1 M NaCl, 0.1% gelatin), these phages constituting in solution the positive BMS maize cell suspension EPSP clones.

4. Preparation and Analysis of the DNA from the BMS Maize Cell Suspension EPSPS Clones.

About 5×10$^8$ phages are added to 20 ml of C600 hfl bacteria at 2 OD 600 nm/ml and incubated for 15 minutes at 37° C. This suspension is then diluted in 200 ml of bacterial growth medium in a 1 l Erlenmeyer flask and stirred in a rotary shaker at 250 rpm. The lysis is assessed by clarification of the medium, corresponding to a lysis of the turbid bacteria and occurs after shaking for about 4 h. This supernatant is then treated as described in "Current Protocols in Molecular Biology". The DNA obtained corresponds to the BMS maize cell suspension EPSP clones.

One to two μg of this DNA are cut with EcoRI and separated on a 0.8% LGTA/TBE agarose gel (ref. CPMB). A final verification consists in ensuring that the purified DNA indeed exhibits a hybridization signal with the Arabidopsis thaliana EPSPS probe. After electrophoresis, the DNA fragments are transferred onto an Amersham Hybond N membrane according to the Southern protocol described in "Current Protocols in Molecular Biology". The filter is hybridized with the Arabidopsis thaliana EPSPS probe according to the conditions described in paragraph 3 above. The clone exhibiting a hybridization signal with the Arabidopsis thaliana EPSPS probe and containing the longest EcoRI fragment has a gel-estimated size of about 1.7 kbp.

5. Production of the pRPA-ML-711 Clone:

Ten μg of DNA from the phage clone containing the 1.7 kbp insert are digested with EcoRI and separated on a 0.8% LGTA/TBE agarose gel (ref. CPMB). The gel fragment containing the 1.7 kbp insert is excised from the gel by BET staining and the fragment is treated with β-agarase according to the protocol of the supplier New a Biolabs. The DNA purified from the 1.7 kbp fragment is ligated at 12° C. for 14 h with the DNA from the plasmid pUC 19 (New England Biolabs) cut with EcoRI according to the ligation protocol described in "Current Protocols in Molecular Biology". Two μl of the above ligation mixture are used for the transformation of an aliquot of electrocompetent E. coli DH10B; the transformation is performed by electroporation using the following conditions: the mixture of competent bacteria and of ligation medium is introduced into an electroporation cuvette 0.2 cm thick (Biorad) previously cooled to 0° C. The physical conditions for the electroporation using an electroporator of Biorad brand are 2,500 volts, 25 μFarad and 200Ω. Under these conditions, the mean condenser discharge time is of the order of 4.2 milliseconds. The bacteria are then taken up in 1 ml of SOC medium (ref. CPMB) and stirred for 1 hour at 200 rpm on a rotary shaker in 15 ml Corning tubes. After plating on LB/agar medium supplemented with 100 μg/ml of carbenicillin, the minipreparations of the bacterial clones which have grown overnight at 37° C. are prepared according to the protocol described in "Current Protocols in Molecular Biology". After digesting the DNA with EcoRI and separating by electrophoresis on a 0.8% LGTA/TBE agarose gel (ref. CPMB), the clones having a 1.7 kbp insert are preserved. A final verification consists in ensuring that the purified DNA indeed exhibits a hybridization signal with the Arabidopsis thaliana EPSPS probe. After electrophoresis, the DNA fragments are transferred onto an Amersham Hybond N membrane according to the Southern protocol described in "Current Protocols in Molecular Biology". The filter is hybridized with the Arabidopsis thaliana EPSPS probe according to the conditions described in paragraph 3 above. The plasmid clone having a 1.7 kbp insert and hybridizing with the Arabidopsis thaliana EPSPS probe was prepared on a larger scale and the DNA resulting from lysing the bacteria purified on a CsCl gradient as described in "Current Protocols in Molecular Biology". The purified DNA was partially sequenced with a Pharmacia kit according to the instructions of the supplier and using, as primers, the reverse and direct M13 universal primers ordered from the same supplier. The partial sequence determined covers about 0.5 kbp. The derived amino acid sequence in the region of the mature protein (about 50 amino acid residues) exhibits 100% identity with the corresponding amino sequence of the mature maize EPSPS described in American patent U.S. Pat. No. 4,971,908). This clone corresponding to a 1.7 kbp EcoRI fragment of the BMS maize cell suspension EPSP DNA was called pRPA-ML-711. The complete sequence of this clone was determined on both strands using the Pharmacia kit protocol and by synthesizing oligonucleotides which are complementary and of opposite direction every 250 bp approximately. The complete sequence of this 1713 bp clone obtained is presented in SEQ ID No. 2.

6. Production of the pRPA-ML-715 Clone:

The analysis of the sequence of the pRPA-ML-711 clone and in particular comparison of the derived amino acid sequence with that from maize shows a 92 bp sequence extension upstream of the GCG codon encoding the $NH_2$-terminal alanine of the mature part of maize EPSPS (American patent U.S. Pat. No. 4,971,908). Likewise, a 288 bp extension downstream of the AAT codon encoding the COOH-terminal asparagine of the mature part of maize EPSPS (American patent U.S. Pat. No. 4,971,908) is observed. These two parts may correspond, for the $NH_2$-terminal extension, to a portion of the sequence of a transit peptide for plastid localization and, for the COOH-terminal extension, to the 3' untranslated region of the cDNA.

To obtain a cDNA encoding the mature part of the maize EPSPS cDNA, as described in U.S. Pat. No. 4,971,908, the following operations were carried out:

a) Elimination of the Untranslated 3' Region: Construction of pRPA-ML-712:

The pRPA-ML-711 clone was cut with the restriction enzyme AseI and the ends resulting from this cut made blunt by treating with the Klenow fragment of DNA polymerase I according to the protocol described in CPMB. A cut with the restriction enzyme SacII was then made. The DNA resulting from these operations was separated by electrophoresis on a 1% LGTA/TBE agarose gel (ref. CPMB).

The gel fragment containing the 0.4 kbp "AseI-blunt ends/SacII" insert was excised from the gel and purified according to the protocol described in paragraph 5 above. The DNA of the clone pRPA-ML-711 was cut with the restriction enzyme HindIII situated in the polylinker of the cloning vector pUC19 and the ends resulting from this cut were made blunt by treating with the Klenow fragment of DNA polymerase I. A cut with the restriction enzyme SacII was then made. The DNA resulting from these manipulations was separated by electrophoresis on a 0.7% LGTA/TBE agarose gel (ref. CPMB).

The gel fragment containing the HindIII-blunt ends/SacII insert of about 3.7 kbp was excised from the gel and purified according to the protocol described in paragraph 5 above.

The two inserts were ligated, and 2 µl of the ligation mixture were used to transform E. coli DH10B as described above in paragraph 5.

The plasmid DNA content of the various clones is analyzed according to the procedure described for pRPA-ML-711. One of the plasmid clones retained contains an EcoRI-HindIII insert of about 1.45 kbp. The sequence of the terminal ends of this clone shows that the 5' end of the insert corresponds exactly to the corresponding end of pRPA-ML-711 and that the 3' terminal end has the following sequence:

"5'-AATTAAGCTCTAGAGTCGACCTGCAG-GCATGCAAGCTT-3'" (SEQ ID NO: 18).

The sequence underlined corresponds to the codon for the COOH-terminal amino acid asparagine, the next codon corresponding to the translational stop codon. The downstream nucleotides correspond to sequence elements of the pUC19 polylinker. This clone comprising the pRPAML-711 sequence up to the site for termination of translation of mature maize EPSPS and followed by pUC19 polylinker sequences up to the HindIII site was called pRPA-ML-712.

b) Modification of the 5' End of pRPA-ML-712: Construction of pRPA-ML-715

The pRPA-ML-712 clone was cut with the restriction enzymes PstI and HindIII. The DNA resulting from these manipulations was separated by electrophoresis on a 0.8% LGTA/TBE agarose gel (ref. CPMB). The gel fragment containing the 1.3 kbp PstI/EcoRI insert was excised from the gel and purified according to the protocol described in paragraph 5 above. This insert was ligated in the presence of an equimolar quantity of each of the two partially complementary oligonucleotides of sequence:

Oligo 1: 5'-GAGCCGAGCTCCATGGCCGGCGC-CGAGGAGATCGTGCTGCA-3' (SEQ ID NO:19)

Oligo 2: 5'-GCACGATCTCCTCGGCGCCGGCCATG-GAGCTCGGCTC-3' (SEQ ID NO:20)

and in the presence of DNA from the plasmid pUC19 digested with the restriction enzymes BamHI and HindIII.

Two µl of the ligation mixture served to transform E. coli DH10B as described above in paragraph 5. After analysis of the plasmid DNA content of various clones according to the procedure described above in paragraph 5, one of the clones having an insert of about 1.3 kbp was preserved for subsequent analyses. The sequence of the terminal 5' end of the clone retained shows that the DNA sequence in this region is the following: pUC19 polylinker sequence of the EcoRI to BamHI sites, followed by the sequence of the oligonucleotides used during the cloning, followed by the remainder of the sequence present in pRPAML-712. This clone was called pRPA-ML-713. This clone has a methionine codon ATG included in an NcoI site upstream of the N-terminal alanine codon of the mature EPSP synthase. Furthermore, the alanine and glycine codons of the N-terminal end were conserved, but modified on the third variable base: initial GCGGGT gives modified GCCGGC.

The clone pRPA-ML-713 was cut with the restriction enzyme HindIII and the ends of this cut made blunt by treating with the Klenow fragment of DNA polymerase I. A cut with the restriction enzyme SacI was then made. The DNA resulting from these manipulations was separated by electrophoresis on a 0.8% LGTA/TBE agarose gel (ref. CPMB). The gel fragment containing the 1.3 kbp "HindIII-blunt ends/SacI" insert was excised from the gel and purified according to the protocol described in paragraph 5 above. This insert was ligated in the presence of DNA from the plasmid pUC19 digested with the restriction enzyme XbaI and the ends of this cut made blunt by treating with the Klenow fragment of DNA polymerase I. A cut with the restriction enzyme SacI was then made. Two µl of the ligation mixture were used to transform E. coli DH10B as described above in paragraph 5. After analysis of the plasmid DNA content of various clones according to the procedure described above in paragraph 5, one of the clones having an insert of about 1.3 kbp was preserved for subsequent analyses. The sequence of the terminal ends of the clone retained shows that the DNA sequence is the following: pUC19 polylinker sequence of the EcoRI to SacI sites, followed by the sequence of the oligonucleotides used during the cloning, deleted of the 4 bp GATCC of oligonucleotide 1 described above, followed by the remainder of the sequence present in pRPA-ML-712 up to the HindIII site and sequence of the pUC19 polylinker from XbaI to HindIII. This clone was called pRPA-ML-715.

7) Production of a cDNA Encoding a Mutated Maize EPSPS

All the mutagenesis stages were performed with the U.S.E. mutagenesis kit from Pharmacia, following the instructions of the supplier. The principle of this mutagenesis system is the following: the plasmid DNA is heat-denatured and annealed in the presence of a molar excess, on the one hand, of the mutagenesis oligonucleotide and, on the other hand, of an oligonucleotide which makes it possible to eliminate a unique restriction enzyme site present in the polylinker. After the annealing stage, the synthesis of the complementary strand is carried out by the action of T4 DNA polymerase in the presence of T4 DNA ligase and protein from gene 32 in an appropriate buffer provided. The synthetic product is incubated in the presence of the restriction enzyme, whose site is supposed to have disappeared by mutagenesis. The *E. coli* strain having, in particular, the muts mutation is used as host for the transformation of this DNA. After growth in liquid medium, the total plasmid DNA is prepared, incubated in the presence of the restriction enzyme previously used. After these treatments, the *E. coli* DH10B strain is used as host for the transformation. The plasmid DNA of the clones isolated is prepared and the presence of the mutation introduced is verified by sequencing.

A)—Sequence or site modifications without any effect a priori on the resistance character of maize EPSPS to products which are competitive inhibitors of the activity of EPSP synthase: elimination of an internal NcoI site from pRPA-ML-715.

The sequence of pRPA-ML-715 is numbered arbitrarily by placing the first base of the N-terminal alanine codon GCC in position 1. This sequence has an NcoI site at position 1217. The site modification oligonucleotide has the sequence:

5'-CCACAGGATGGCGATGGCCTTCTCC-3' (SEQ ID NO:21).

After sequencing according to the references given above, the sequence read after mutagenesis corresponds to that of the oligonucleotide used. The NcoI site was indeed eliminated and the translation into amino acids in this region conserves the initial sequence present in pRPA-ML-715.

This clone was called pRPA-ML-716.

The 1340 bp sequence of this clone is presented SEQ ID No. 3 and SEQ ID No. 4.

B) Sequence modifications allowing an increase in the resistance character of maize EPSPS to products which are competitive inhibitors of EPSP synthase activity.

The following oligonucleotides were used:
a) Thr 102→Ile mutation.
5'-GAATGCTGGAATCGCAATGCGGCCAT-TGACAGC-3' (SEQ ID NO:22)
b) Pro 106→Ser mutation.
5'-GAATGCTGGAACTGCAATGCGGTCCT-TGACAGC-3' (SEQ ID NO:23)
c) Gly 101→Ala and Thr 102→Ile mutations.
5'-CTTGGGGAATGCTGCCATCGCAATGCG-GCCATTG-3' (SEQ ID NO:24)
d) Thr 102→Ile and Pro 106→Ser mutations.
5'-GGGGAATGCTGGAATCGCAATGCGGTC-CTTGACAGC-3' (SEQ ID NO:25)

After sequencing, the sequence read after mutagenesis on the three mutated fragments is identical to the parental DNA sequence pRPA-ML-716 with the exception of the mutagenized region which corresponds to that of the mutagenesis oligonucleotides used. These clones were called: pRPA-ML-717 for the Thr 102→Ile mutation, pRPA-ML-718 for the Pro 106→Ser mutation, pRPA-ML-719 for the Gly 101→Ala and Thr 102→Ile mutations and pRPA-ML-720 for the Thr 102→Ile and Pro 106→Ser mutations.

The 1340 bp sequence of pRPA-ML-720 is presented SEQ ID No. 5 and SEQ ID No. 6.

The 1395 bp NcoI-HindIII insert forms the basis of all the constructs used for the transformation of the plants for the introduction of the resistance to herbicides which are competitive inhibitors of EPSPS and in particular the resistance to glyphosate. This insert will be called in the remainder of the descriptions "the double maize EPSPS mutant".

B Glyphosate Tolerance of the Various Mutants in Vitro.

2.a: Extraction of EPSP synthase.

The various EPSP synthase genes are introduced in the form of an NcoI-HindIII cassette into the plasmid vector pTrc99a (Pharmacia, ref: 27-5007-01) cut with NcoI and HindIII. The recombinant *E. coli* DH10B overexpressing the various EPSP synthases are sonicated in 40 ml of buffer per 10 g of culotted cells and washed with this same buffer (200 mM Tris-HCl pH 7.8, 50 mM mercaptoethanol, 5 mM EDTA and 1 mM PMSF), to which 1 g of polyvinylpyrrolidone is added. The suspension is stirred for 15 minutes at 4° C. and then centrifuged for 20 minutes at 27,000 g and at 4° C.

The supernatant is supplemented with ammonium sulphate so as to bring the solution to 40% saturation with ammonium sulphate. The mixture is centrifuged for 20 minutes at 27,000 g and at 4° C. The new supernatant is supplemented with ammonium sulphate so as to bring the solution to 70% saturation with ammonium sulphate.

The mixture is centrifuged for 30 minutes at 27,000 g and at 4° C. The EPSP synthase present in this protein pellet is taken up in 1 ml of buffer (20 mM Tris-HCl pH 7.8 and 50 mM mercaptoethanol). This solution is dialysed overnight against two liters of this same buffer at 4° C.

2.b: Enzymatic Activity.

The activity of each enzyme as well as its resistance to glyphosate is measured in vitro over 10 minutes at 37° C. in the following reaction mixture: 100 M maleic acid pH 5.6, 1 mM phosphoenol pyruvate, 3 mM shikimate-3-phosphate (prepared according to Knowles P. F. and Sprinson D. B., 1970, Methods in Enzymol., 17A, 351-352 from *Aerobacter aerogenes* strain ATCC 25597) and 10 mM potassium fluoride. The enzymatic extract is added at the last moment after the addition of glyphosate whose final concentration varies from 0 to 20 mM.

The activity is measured by assaying the phosphate liberated according to the technique of Tausky H. A. and Shorr E., 1953, J. Biol. Chem., 202, 675-685.

Under these conditions, the wild-type (WT) enzyme is 85% inhibited starting from the concentration of 0.12 mM glyphosate. At this concentration, the mutant enzyme known as Ser106 is only 50% inhibited and the other three mutants Ile 102, Ile 102/Ser 106, Ala 101/Ile 102 are not or not strongly inhibited.

The glyphosate concentration should be multiplied by ten, that is to say 1.2 mM, in order to inhibit the mutant enzyme Ile 102 by 50%, the mutants Ile 102/Ser 106, Ala/Ile and Ala still not being inhibited.

It should be noted that the activity of the Ala/Ile and Ala mutants is not inhibited up to concentrations of 10 mM glyphosate, and that that of the mutant Ile 102/Ser 106 is not reduced even when the glyphosate concentration is multiplied by 2, that is to say 20 mM.

C Resistance of the Transformed Tobacco Plants.

0-1 Construction of the Plasmids:

pRPA-RD-124: Addition of a "nos" polyadenylation signal to pRPA-ML-720, previously obtained, with creation of a cloning cassette containing the maize double mutant EPSPS gene (Thr 102 Ile and Pro 106→Ser). pRPA-ML-720 is digested with HindIII, treated with the Klenow fragment of DNA polymerase from *E. coli* in order to produce a blunt end. A second digestion is carried out with NcoI and the EPSPS fragment is purified. The EPSPS gene is then ligated with purified pRPA-RD-12 (a cloning cassette containing the nopaline synthase polyadenylation signal) in order to give pRPA-RD-124. In order to obtain the useful purified vector pRPA-RD-12, it was necessary that the latter be previously digested with SalI, treated with Klenow DNA polymerase and then digested a second time with NcoI.

pRPA-RD-125: Addition of an optimized transit peptide (OTP) to pRPA-RD-124 with creation of a cloning cassette containing the targeted EPSPS gene on the plasmids. pRPA-RD-7 (European Patent Application EP 652 286) is digested with SphI, treated with T4 DNA polymerase, and then digested with SpeI and the OTP fragment is purified. This OTP fragment is cloned into pRPA-RD-124 which was previously digested with NcoI, treated with Klenow DNA polymerase in order to remove the 3' protruding part, and then digested with SpeI. This clone was then sequenced in order to ensure is correct translational fusion between OTP and the EPSPS gene. pRPA-RD-125 is thus obtained.

pRPA-RD-159: Addition of the *Arabidopsis* H4A748 double histone promoter (Patent Application EP 507 698) to pRPA-RD-125 with creation of a cassette for expression in plants for the expression of the gene "OTP-double mutant EPSPS gene" in dicotyledonous tissues. pRPA-RD-132 (a cassette containing the H4A748 double promoter (Patent Application EP 507 698)) is digested with NcoI and SacI. The purified fragment of the promoter is then cloned into what was digested with EcoI and SacI.

pRPA-RD-173: Addition of the gene "promoter of the H4A748-OTP-double mutant EPSPS gene" of pRPA-RD-159 into the plasmid pRPA-BL-150A (European Patent Application 508 909) with creation of an *Agrobacterium tumefaciens* transformation vector. pRPA-RD-159 is digested with NotI and treated with the Klenow polymerase. This fragment is then cloned into pRPA-BL-150A with SmaI.

1-1—Transformation.

The vector pRPA-RD-173 is introduced into the *Agrobacterium tumefaciens* EHA101 strain (Hood et al., 1987) carrying the cosmid pTVK291 (Komari et al., 1986). The transformation technique is based on the procedure of Horsh et al. (1985).

1-2—Regeneration.

The regeneration of the PBD6 tobacco (source SEITA France) from foliar explants is carried out on a Murashige and Skoog (MS) basal medium comprising 30 g/l of sucrose and 200 µg/ml of kanamycin. The foliar explants are removed from greenhouse plants or in vitro and transformed according to the foliar disc technique (Science, 1985, Vol. 227, p. 1229-1231) in three successive stages: the first comprises the induction of shoots on an MS medium supplemented with 30 g/l of sucrose containing 0.05 mg/l of naphthylacetic acid (ANA) and 2 mg/l of benzylaminopurine (BAP) for 15 days. The shoots formed during this stage are then developed by culturing on an MS medium supplemented with 30 g/l of sucrose but containing no hormone, for 10 days. The shoots that have developed are then removed and they are cultured on MS rooting medium with half the content of salts, vitamins and sugar and containing no hormone. After about 15 days, the rooted shoots are planted in the soil.

1-3—Resistance to Glyphosate.

Twenty transformed plants were regenerated and placed in a greenhouse for the construct pRPA-RD-173. These plants were treated in a greenhouse at the 5-leaf stage with an aqueous suspension of RoundUp corresponding to 0.8 kg of glyphosate active substance per hectare.

The results correspond to the observation of phytotoxicity indices noted 3 weeks after the treatment. Under these conditions, it is observed that the plants transformed with the construct pRPA-RD-173 exhibit a very good tolerance whereas the nontransformed control plants are completely destroyed.

These results show clearly the improvement made by the use of a chimeric gene according to the invention for the same gene encoding glyphosate tolerance.

EXAMPLE 5

Transformation of the Industrial Tobacco PBD6, with the Nitrilase Gene (for→Construct 238)

This tobacco is obtained according to the teaching of European Application No. 0 337 899 page 6 line 50 and subsequent pages from the construct 238, which is that described under the name pRPA-BL 238.

EXAMPLE 6

Crossing by Pollination

The lines Co 17, 173 and 238 are crossed respectively by pollination in a greenhouse:
Co 17 with 238 in order to obtain PBD6 tobacco plants to be tested for the double tolerance to isoxaflutole and to bromoxynil ("plants HPPD+OXY") and
Co 17 with 173 in order to obtain PBD6 tobacco plants to be tested for double tolerance to isoxaflutole and glyphosate ("plants HPPD+EPSPS").
The three lines are homozygous with respect to the relevant gene: consequently, the progeny is hemizygous for each of the two genes introduced by crossing.
The crossed plants are obtained after six weeks.

EXAMPLE 7

Measurement of the Tolerance of Tobacco in Postemergence Treatment with Isoxaflutole and Postemergence Treatment with Bromoxynil or Glyphosate In this trial, each test is performed on a sample of 10 plants, 10 plants being kept untreated.

All the treatments are performed by spraying at the rate of 500 l of spraying mixture per hectare.

For the postemergence treatment, sowing is performed and then the plants are transplanted in 9 cm×9 cm pots.

The postemergence treatments are carried out at a well developed stage (3-4 leaves). Batches of plants, respectively wild-type and genetically transformed, obtained above are divided into several parts, with:

a) an untreated batch, b) other batches which are treated respectively with one herbicide alone,
isoxaflutole in postemergence, at two doses (200 and 400 g/ha respectively),
bromoxynil in postemergence at two doses (400 and 800 g/ha respectively),
glyphosate in postemergence at two doses (800 and 1200 g/ha respectively), c) other batches which are treated respectively with two herbicides, in postemergence, in a freshly prepared mixture:
isoxaflutole and bromoxynil at two doses (200/400 and 400/800 g/ha respectively)
isoxaflutole and glyphosate at two doses (200/800 and 400/1200 g/ha respectively).
The treatments are carried out with the following formulations: 75% isoxaflutole, bromoxynil (commercial product PARDNER) in octanoate form as an emulsifiable concentrate at 225 g/l and glyphosate (RoundUp).

Under these conditions, the following phytotoxicities are observed 17 days after the treatment, expressed as percentage destruction indicated in the following table, as well as the number of plants per batch and the doses of herbicide(s) expressed in gram of active substance per hectare:

| | | Postemergence treatment with isoxaflutole and postemergence treatment with bromoxynil or glyphosate | | | | | |
|---|---|---|---|---|---|---|---|
| | | Plants with tolerance gene | | | | | |
| Herbicide in g/l | | * | HPPD + OXY | * | HPPD + EPSPS | * | WITHOUT = wild-type |
| Controls | | 10 | | 10 | | 10 | |
| isoxaflutole alone | 200 | 20 | 4% | 20 | 2% | 10 | 75% |
| | 400 | 20 | 5% | 20 | 3% | 10 | 85% |
| bromoxynil alone | 400 | 10 | 3% | | | 10 | 0% |
| | 800 | 10 | 0% | | | 10 | 0% |
| glyphosate alone | 800 | | | 20 | 0% | 10 | 100% |
| | 1200 | | | 20 | 0% | 10 | 100% |
| isoxaflutole + bromoxynil | 200 400 | 20 | 20% | | | 10 | 100% |
| isoxaflutole + bromoxynil | 400 800 | 20 | 30% | | | 10 | 100% |
| isoxaflutole + glyphosate | 200 800 | | | 40 | 5% | 10 | 100% |
| isoxaflutole + glyphosate | 400 1200 | | | 40 | 10% | 10 | 100% |

*number of plants

EXAMPLE 8

With the aim of studying whether the *Pseudomonas fluorescens* HPPD gene can be used as marker gene during the "transformation-regeneration" cycle of a plant species, the tobacco was transformed with the chimeric gene composed of the HPPD gene and the EPSPS gene doubly mutated for resistance to glyphosate and transformed plants resistant to both isoxaflutole and glyphosate were obtained after selection on isoxaflutole.

Materials and Methods and Results

The chimeric gene pRP 2012 described below is transferred into the PBD6 industrial tobacco according to the transformation and regeneration procedures already described in European Application EP No. 0 508 909.

The chimeric gene of the vector pRP 2012 has the following structure A-B, in which:

A is:

| Double histone promoter | TEV | OTP | Coding region of HPPD | Nos terminator |
|---|---|---|---|---| and B is:

| Double histone promoter | TEV | OTP | Coding region of EPSPS | Nos terminator |
|---|---|---|---|---| such as that used in the vector pRPA-RD-173.

The chimeric gene pRP 2012 is introduced into the tobacco.

1) Transformation:

The vector is introduced into the non-oncogenic *Agrobacterium* EHA 101 strain (Hood et al., 1987) carrying the cosmid pTVK 291 (Komari et al., 1986). The transformation technique is based on the procedure by Horsh et al., (1985).

2) Regeneration:

The regeneration of the PBD6 tobacco (source SEITA France) from foliar explants is carried out on a Murashige and Skoog (MS) basal medium comprising 30 g/l of sucrose and 350 mg/l of cefotaxime and 1 mg/l of isoxaflutole. The foliar explants are removed from greenhouse plants or in vitro and transformed according to the foliar disc technique (Science 1985, Vol. 227, p. 1229-1231) in three successive stages: the first comprises the induction of shoots on an MS medium supplemented with 30 g/l of sucrose containing 0.05 mg/l of naphthylacetic acid (ANA) and 2 mg/l of benzylaminopurine (BAP) for 15 days and 1 mg/l of isoxaflutole. The green shoots formed during this stage are then developed by culturing on an MS medium supplemented with 30 g/l of sucrose and 1 mg/l of isoxaflutole but containing no hormone, for 10 days. The shoots that have developed are then removed and they are cultured on MS rooting medium with half the content of salts, vitamins and sugars and 1 mg/l of isoxaflutole and containing no hormone. After about 15 days, the rooted shoots are planted in the soil.

All the plants obtained according to this protocol are analysed by PCR with primers specific for *P. fluorescens* HPPD. This PCR analysis made it possible to confirm that all the plants thus obtained have indeed integrated the HPPD gene and that they are tolerant to both isoxaflutole and glyphosate, under the conditions described in Example 7.

In conclusion, this trial confirms that the HPPD gene may be used as marker gene and that, combined with this gene, isoxaflutole may be a good selection agent.

EXAMPLE 9

Plant with an HPPD Gene and a Bar Gene Resistant to Both Isoxaflutole and Phosphinothricin 1. Construction of a Chimeric Gene with an HPPD Sequence:

The plasmid pRPA-RD-1004 is obtained by inserting the chimeric gene for resistance to the isoxazoles into the 2686 bp plasmid pUC19, marketed by New England Biolabs (Yanisch-Perron, C., Vieira, J. and Messing, J. (1985) Gene 33, 103-119) and containing the resistance to ampicillin.

The various elements of the chimeric gene are, in the direction of translation:

the 1020 bp maize H3C4 histone promoter described in the application EP 0 507 698;

the intron of the maize alcohol dehydrogenase 1 gene described by Sachs M. et al., Genetics 113: 449-467 (1986) and consisting of 536 bp the optimized transit peptide (OTP) described in Patent Application EP 0 508 909; this OTP consists of the 171 bp of the transit peptide of the small subunit of ribulose 1,5-bisphosphate carboxylase/oxygenase from *Helianthus annuus* (Waksman G. et al., 1987, Nucleics acids Res. 15: 7181) followed by the 66 bp of the mature part of the small subunit of ribulose 1,5-bis-phosphate carboxylase/oxygenase from *Zea mays* (Lebrun et al., 1987, Nucleics acids Res. 15: 4360), themselves followed by the 150 bp of the transit peptide of the small subunit of ribulose 1,5-bisphosphate carboxylase/oxygenase from *Zea mays* (Lebrun et al., 1987, Nucleics acids Res. 15: 4360); the whole is therefore 387 bp;

the coding region of the *Pseudomonas fluorescens* HPPD described above;

the terminator of the nopaline synthase (nos) gene (polyadenylation region of the nos gene isolated from pTi 37, 250 bp (Bevan M. et al., Nucleics Acids Res. 11: 369-385);

2. Construction of a Chimeric Gene for Tolerance to Phosphinothricin (Bar Gene):

Phosphinothricin acetyl transferase (PAT) encoded by the bar gene is an enzyme which inactivates a herbicide, phosphinothricin (PPT). PPT inhibits the synthesis of glutamine and causes rapid accumulation of ammonia in the cells, leading to their death (Tachibana et al., 1986).

The plasmid used to introduce the tolerance to phosphinothricin as selection agent is obtained by inserting the chimeric gene pDM 302 into the 2462 bp vector pSP72, marketed by Promega Corp. (Genbank/DDBJ database accession number X65332) and containing the gene for resistance to amplicillin.

The 4700 bp plasmid pDM 302 has been described by Cao, J., et al., Plant Cell Report 11: 586-591 (1992).

The various elements of this plasmid are:

the promoter of the rice actin gene described by McElroy D. et al., Plant Molecular Biology 15: 257-268 (1990) consisting of 840 bp;

the first exon of the rice actin gene consisting of 80 bp;

the first intron of the rice actin gene consisting of 450 bp;

—the coding region of the bar gene of 600 bp excised from the plasmid plJ41404 described by White J. et al., Nuc. Acids res. 18: 1862 (1990);

the terminator of the nopaline synthase (nos) gene (polyadenylation region of the nos gene isolated from pTi 37, 250 bp (Bevan M. et al., Nucleics Acids Res. 11: 369-385).

3. Transformation:

The bombardment technique is used to introduce the genetic construct. The plasmids are purified on a Qiagen column and coprecipitated on particles of tungsten M10 according to the Klein process (Nature 327: 70-73, 1987).

A mixture of metallic particles and of the two plasmids described above is then bombarded on maize embryogenesis cells according to the protocol by 4. Regeneration and Use of the Bar Gene as Selection Agent:

The bombarded calli are selected on glufosinate until green sectors appear. The positive calli are then converted into somatic embryos and then placed under conditions promoting germination. The young plants are transferred into a greenhouse for the production of seeds.

The molecular analyses carried out on these plants show that:

at least 4 calli selected on phosphinothricin generated plants showing the presence of the HPPD gene by PCR;

at least 5 calli selected on phosphinothricin generated plants showing the presence of the HPPD gene by Southern blotting;

at least 5 calli selected on phosphinothricin generated plants showing the presence of the recombinant protein by Western blotting;

the HPPD chimeric gene and the heterologous protein are absent from the nontransformed calli.

These results show the efficiency of the bar chimeric gene for the selection of the transformed calli containing another gene of agronomic interest.

5. Analysis of the Progeny of the Transformed Plants:

The transformed plants obtained above produced pollen, assumed in part to be transgenic, which fertilized ovules from a nontransgenic wild-type maize. The seeds obtained are selected on sand after treating with isoxaflutole.

The selection protocol is the following: is 800 ml of Fontainebleau sand are placed in a tub with sides 15×20 cm. These tubs are then sprayed with water and kept hydrated by supplying a nutritive solution consisting of 5 ml of Quinoligo (Quinoline) per liter of water. Twenty maize seeds are placed on the tubs, which are then treated with isoxaflutole by spraying at the rate of 100 to 200 g of active substance per hectare (300 or 600 µg of active substance per tub). The tubs are then placed in culture in a greenhouse.

The results obtained are assembled in the following table:

| Genotypes | Isoxaflutole (g/ha) | Number of seeds sown | Number of germinated plants | Number of dead plants | Number of surviving plants |
|---|---|---|---|---|---|
| nontransgenic | 0 | 20 | 20 | 0 | 20 |
|  | 100 | 20 | 20 | 20 | 0 |
| 261 2B 459 | 100 | 10 | 10 | 5 | 5 |
|  | 200 | 10 | 9 | 4 | 5 |
| 261 2D2 | 100 | 10 | 9 | 6 | 3 |
|  | 200 | 10 | 10 | 7 | 3 |
| 261 2A2 | 100 | 10 | 5 | 3 | 2 |
|  | 200 | 10 | 7 | 7 | 0 |

These results show the efficiency of the HPPD gene for the selection of resistant maize plants. They also show that the overexpression of *Pseudomonas* HPPD in maize tissues confers the tolerance to isoxaflutole on them.

The sequences illustrated are the following:

SEQ ID No. 1

Sequence of the HPPD gene from *Pseudomonas fluorescens* A32.

SEQ ID No. 2

Sequence of the *Arabidopsis thaliana* EPSPS cDNA

SEQ ID No. 3 and 4

Sequences, respectively, of the gene and of the protein for the mutated maize EPSPS, 1340 bp portion of the clone pRPA-ML-716

SEQ ID No. 5 and SEQ ID No. 6

Sequences, respectively, of the gene and of the protein for the mutated maize EPSPS, 1340 bp portion of the clone pRPA-ML-720

The figures below are given as a guide to illustrate the invention.

FIG. 1 represents the protein sequence of the HPPD from *Pseudomonas* sp. strain P.J. 874 (SEQ ID NO: 26) and the theoretical nucleotide sequence of the corresponding coding part (SEQ ID NO: 27); the five oligonucleotides chosen to perform the amplification of a portion of this coding region are symbolized by the five arrows.

Figure 2:
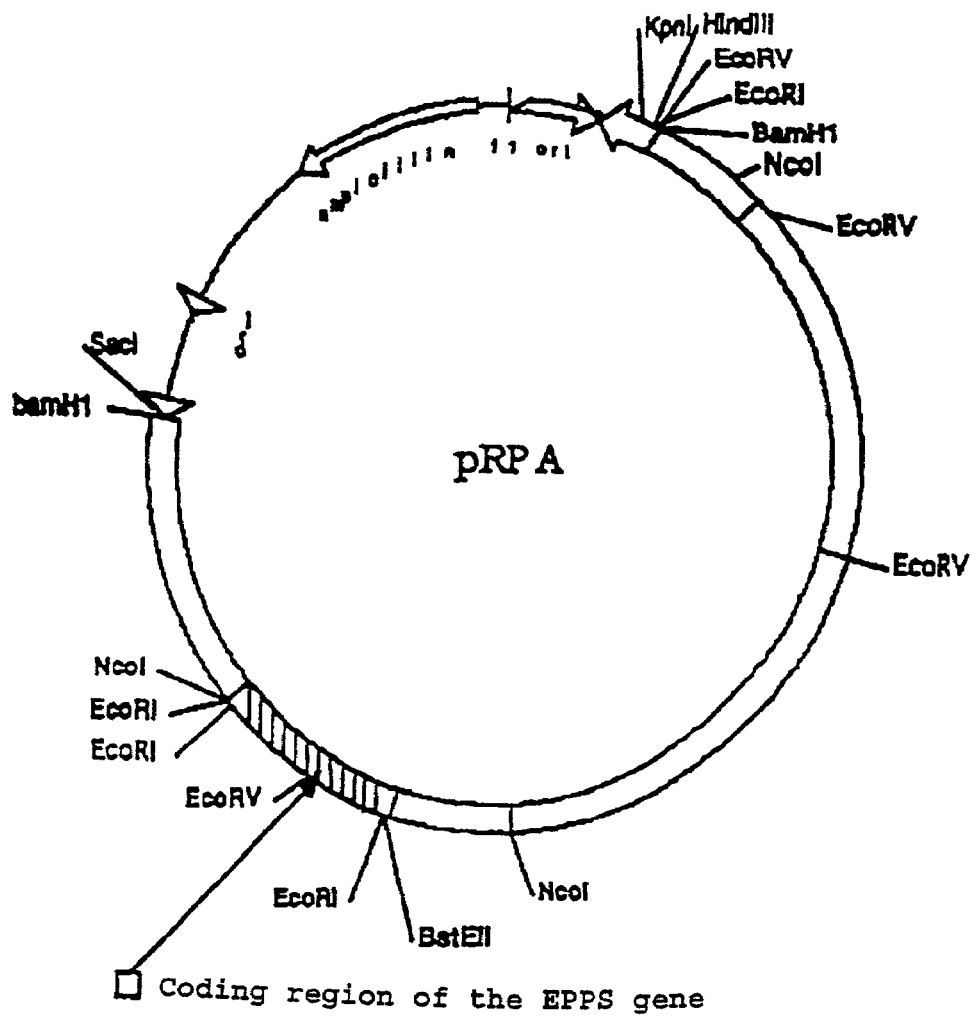
FIG. 2 represents the map of the plasmid with the 7 kb genomic DNA fragment containing the HPPD gene from *P. fluorescens* A32.

FIG. 3 gives the comparison of the amino acid sequences of the HPPD from *P. fluorescens* A32 and of the HPPD from *Pseudomonas* sp. strain P.J. 874 (only the amino acids diverging between the two sequences are indicated) as well as the consensus sequence (SEQ ID NO. 28).

The invention claimed is:

1. A chimeric gene comprising at least two basic chimeric genes each comprising regulatory elements necessary for its transcription in plants and a coding sequence encoding an enzyme conferring on plants the tolerance to a herbicide, characterized in that one of the coding sequences encodes hydroxyphenyl pyruvate dioxygenase (HPPD).

2. The chimeric gene according to claim 1, characterized in that it comprises, in addition, a third chimeric gene containing a sequence encoding an enzyme conferring herbicide tolerance on plants.

3. The chimeric gene according to claim 2, characterized in that the second coding sequence encodes an EPSPS conferring tolerance to a herbicide inhibiting EPSPS.

4. The chimeric gene according to claim 1, characterized in that the second coding sequence encodes tolerance to glyphosate.

5. The chimeric gene according to claim 4, characterized in that the second coding sequence encodes an EPSPS conferring tolerance to glyphosate.

6. The chimeric gene according to claim 4, characterized in that the second coding sequence encodes glyphosate oxidoreductase, an enzyme for detoxification of glyphosate.

7. The chimeric gene according to claim 2, characterized in that the sequence encoding HPPD is derived from *Pseudomonas* sp.

8. The chimeric gene according to claim 7, characterized in that the sequence encoding HPPD is derived from *Pseudomonas fluorescens*.

9. The chimeric gene according to claim 2, characterized in that the sequence encoding HPPD is of plant origin.

10. The chimeric gene according to claim 9, characterized in that the sequence encoding HPPD is derived from *Arabidopsis thaliana*.

11. The chimeric gene according to claim 9, characterized in that the sequence encoding HPPD is derived from *Daucus carota*.

12. A vector characterized in that it comprises the chimeric gene according to claim 1.

13. The vector according to claim 12, characterized in that it consists of a plasmid.

14. A plant cell transformed with at least two chimeric genes each containing a coding sequence encoding an enzyme conferring on plants tolerance to a herbicide, wherein one of said coding sequences encodes hydroxyphenyl pyruvate dioxygenase (HPPD).

15. The plant cell according to claim 14, characterized in that it contains three basic chimeric genes each containing regulatory elements and a coding sequence encoding an enzyme conferring on plants the tolerance to a herbicide.

16. The plant cell according to claim 14, wherein said plant cell contains at least one chimeric gene.

17. A plant which contains the plant cell according to claim 14.

18. A process for transforming plants to make them tolerant to at least two herbicides, said process comprising the steps of transforming a plant cell with the chimeric gene of claim 1 and regenerating a plant from the transformed plant cell.

* * * * *